US010113906B2

(12) United States Patent
Labrie et al.

(10) Patent No.: US 10,113,906 B2
(45) Date of Patent: *Oct. 30, 2018

(54) DEVICES AND METHODS FOR MEASURING LIGHT

(71) Applicant: BlueLight Analytics, Inc., Halifax (CA)

(72) Inventors: Daniel Labrie, Halifax (CA); Ivan Kostylev, Bedford (CA); Chris Felix, Beaver Bank (CA)

(73) Assignee: BlueLight Analytics, Inc., Halifax (CA)

( * ) Notice: Subject to any disclaimer, the term of this patent is extended or adjusted under 35 U.S.C. 154(b) by 223 days.

This patent is subject to a terminal disclaimer.

(21) Appl. No.: 15/093,184

(22) Filed: Apr. 7, 2016

(65) Prior Publication Data

US 2017/0067777 A1    Mar. 9, 2017

Related U.S. Application Data

(63) Continuation of application No. 14/022,783, filed on Sep. 10, 2013, now Pat. No. 9,310,298.
(Continued)

(51) Int. Cl.
*G01N 21/47* (2006.01)
*G01J 1/04* (2006.01)
(Continued)

(52) U.S. Cl.
CPC .......... *G01J 1/0474* (2013.01); *A61C 19/003* (2013.01); *G01J 1/0204* (2013.01); *G01J 1/0219* (2013.01);
(Continued)

(58) Field of Classification Search
CPC .. G01N 21/474; G01N 21/4738; G01N 21/55; G01N 21/57; G01N 21/8483
(Continued)

(56) References Cited

U.S. PATENT DOCUMENTS

| 4,915,500 A |   | 4/1990 | Selkowitz |
|---|---|---|---|
| 5,800,184 A | * | 9/1998 | Lopergolo ........... H05K 7/1069 439/591 |

(Continued)

FOREIGN PATENT DOCUMENTS

| DE | 2417399 A1 | 10/1975 |
|---|---|---|
| JP | 2003-214946 A | 7/2003 |

(Continued)

OTHER PUBLICATIONS

Extended European Search Report for European Patent Application 13835832.0, dated Nov. 24, 2016 (19 pages).
(Continued)

*Primary Examiner* — Md M Rahman
(74) *Attorney, Agent, or Firm* — Clark & Elbing LLP

(57) ABSTRACT

The invention features devices and methods for collecting and measuring light from external light sources. In general, the devices of the invention feature a light diffusing element, e.g., as a component of a light collector, connected by a light conducting conduit, e.g., a fiber optic cable, to a light measuring device, e.g., a spectrometer. This light diffusing element allows, e.g., for substantially uniform light diffusion across its surface and thus accurate measurements, while permitting the total footprint of the device to remain relatively small and portable. This light diffusing element also allows flexibility in scaling of the device to permit use in a wide range of applications.

22 Claims, 29 Drawing Sheets

Related U.S. Application Data

(60) Provisional application No. 61/784,827, filed on Mar. 14, 2013, provisional application No. 61/698,995, filed on Sep. 10, 2012.

(51) Int. Cl.

| | |
|---|---|
| *G01M 11/02* | (2006.01) |
| *G02B 5/02* | (2006.01) |
| *G01N 21/55* | (2014.01) |
| *G01J 3/02* | (2006.01) |
| *A61C 13/15* | (2006.01) |
| *G01J 1/02* | (2006.01) |
| *G01J 1/42* | (2006.01) |

(52) U.S. Cl.
CPC ............ *G01J 1/0271* (2013.01); *G01J 1/0425* (2013.01); *G01J 1/0488* (2013.01); *G01J 3/0205* (2013.01); *G01J 3/0218* (2013.01); *G01J 3/0254* (2013.01); *G01J 3/0256* (2013.01); *G01J 3/0264* (2013.01); *G01M 11/0235* (2013.01); *G01N 21/55* (2013.01); *G02B 5/02* (2013.01); *G02B 5/021* (2013.01); *G02B 5/0284* (2013.01); *G01J 2001/0481* (2013.01); *G01J 2001/4247* (2013.01)

(58) Field of Classification Search
USPC ......................................................... 356/446
See application file for complete search history.

(56) References Cited

U.S. PATENT DOCUMENTS

| | | | | |
|---|---|---|---|---|
| 6,292,003 B1* | 9/2001 | Fredrickson | ......... | G01R 1/0483 324/750.25 |
| 6,437,861 B1 | 8/2002 | Kuta | | |
| 6,468,077 B1* | 10/2002 | Melikechi | ............ | A61C 19/004 433/215 |
| 6,710,798 B1* | 3/2004 | Hershel | .............. | G01R 31/2887 324/750.23 |
| 8,078,256 B2* | 12/2011 | Zan | ...................... | A61B 8/0833 219/218 |
| 9,310,298 B2* | 4/2016 | Labrie | .................. | A61C 19/003 |
| 9,684,052 B2* | 6/2017 | Olmstead | ............... | G01R 35/00 |
| 2001/0022342 A1 | 9/2001 | Wirthlin | | |
| 2001/0038453 A1 | 11/2001 | Jung et al. | | |
| 2003/0146663 A1* | 8/2003 | Nelson | ..................... | G01J 1/08 307/11 |
| 2005/0116178 A1 | 6/2005 | Aguirre et al. | | |
| 2006/0244907 A1 | 11/2006 | Simmons | | |
| 2007/0037113 A1 | 2/2007 | Scott et al. | | |
| 2007/0053043 A1* | 3/2007 | Wada | ........................ | B41J 2/473 359/216.1 |
| 2007/0096763 A1* | 5/2007 | Ehrmann | ............ | G01R 31/2891 324/750.23 |
| 2007/0224570 A1 | 9/2007 | West et al. | | |
| 2008/0197865 A1* | 8/2008 | Endres | ................ | G01R 31/2886 324/754.07 |
| 2009/0290902 A1* | 11/2009 | Amico | ................ | G03G 15/5016 399/107 |
| 2010/0176831 A1* | 7/2010 | Palcisko | ............ | G01R 1/07378 324/756.03 |
| 2011/0108741 A1 | 5/2011 | Ingram | | |
| 2011/0205541 A1 | 8/2011 | Osawa et al. | | |
| 2011/0267087 A1* | 11/2011 | Huang | ............... | G01R 31/2635 324/754.23 |
| 2011/0275900 A1 | 11/2011 | Gilhuly et al. | | |
| 2012/0026307 A1 | 2/2012 | Price | | |
| 2012/0171745 A1 | 7/2012 | Itoh | | |
| 2012/0172478 A1 | 7/2012 | Chang et al. | | |
| 2012/0196122 A1 | 8/2012 | Bishop et al. | | |
| 2013/0207550 A1* | 8/2013 | Nishio | ................... | G05D 25/02 315/151 |
| 2014/0092716 A1* | 4/2014 | Saito | ...................... | B82Y 35/00 369/53.38 |
| 2015/0177313 A1* | 6/2015 | Hoelter | .............. | G02B 27/0977 324/754.21 |
| 2016/0265747 A1* | 9/2016 | Nagao | ................... | A61B 1/0684 |
| 2017/0031516 A1* | 2/2017 | Sugiyama | ............. | G06F 3/0416 |
| 2017/0179682 A1* | 6/2017 | Ishii | ....................... | H01S 5/0262 |
| 2017/0199271 A1* | 7/2017 | Nihei | .................... | G01S 7/4808 |
| 2017/0235059 A1* | 8/2017 | Anderson | ............ | G02B 6/3696 385/126 |
| 2017/0259763 A1* | 9/2017 | Chassard | ............ | B60R 16/0231 |
| 2017/0293067 A1* | 10/2017 | Watanabe | ............ | G02B 6/0033 |
| 2017/0293812 A1* | 10/2017 | Itoh | ........................ | G01N 21/21 |

FOREIGN PATENT DOCUMENTS

| | | |
|---|---|---|
| JP | 2010-139446 A | 6/2010 |
| JP | 2011-174785 A | 9/2011 |
| WO | WO-2010/115274 A1 | 10/2010 |
| WO | WO-2014/036660 A1 | 3/2014 |

OTHER PUBLICATIONS

Henry Schein, Inc., "Henry Schein Canada first to offer dentists curing light testing service by bluelight analytics," News Release, dated Jul. 9, 2014 (3 pages).
International Search Report and Written Opinion for International Application No. PCT/CA2013/050694, dated Nov. 18, 2013 (9 pages).
JCDA Oasis, "An EnLIGHTening look at light sources in dentistry," <http://www.oasisdiscussions.ca/2014/07/17/cl-2/>, retrieved on Aug. 13, 2014 (3 pages).
Leonard et al., "Effect of curing-tip diameter on the accuracy of dental radiometers," Oper Dent. 24(1):31-7 (1999).
Office Action from Japanese Patent Application No. 2015-530253, dated Jun. 27, 2017 (8 pages).
Partial Supplementary European Search Report for European Application No. 13835832.0, dated Jun. 23, 2016 (8 pages).
Price et al., "Intra- and inter-brand accuracy of four dental radiometers," Clin Oral Investig. 16(3):707-17 (2012).
Roberts et al., "Accuracy of LED and halogen radiometers using different light sources," J Esthet Restor Dent. 18(4):214-22 (2006).
Shortall et al., "Robust spectrometer-based methods for characterizing radiant exitance of dental LED light curing units," Dent Mater. 31(4):339-50 (2015).
"Some of the challenges that prevent radiometers from providing an accurate or relevant irradiance measurement," BlueLight Analytics Inc., received Aug. 15, 2014 (5 pages).

* cited by examiner

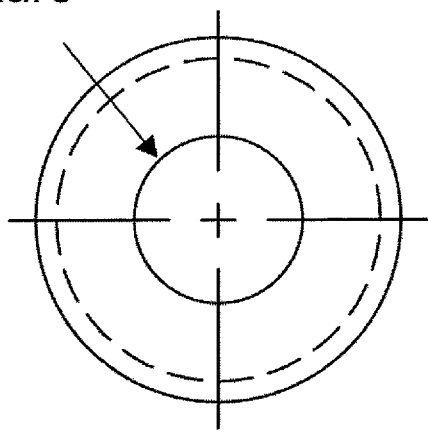
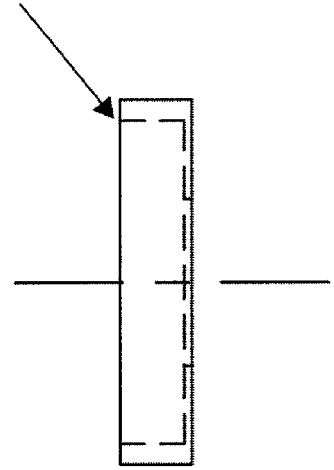
Figure 5A
Figure 5B

Figure 15A
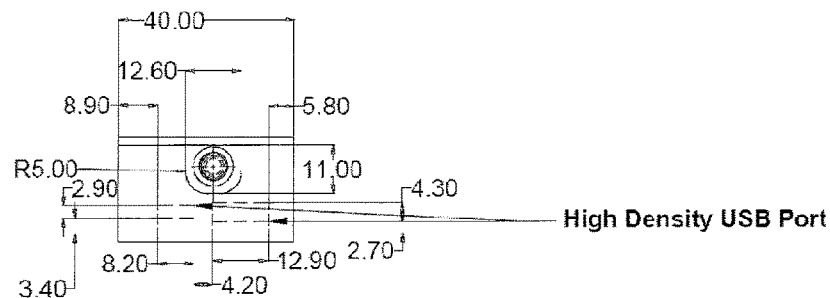
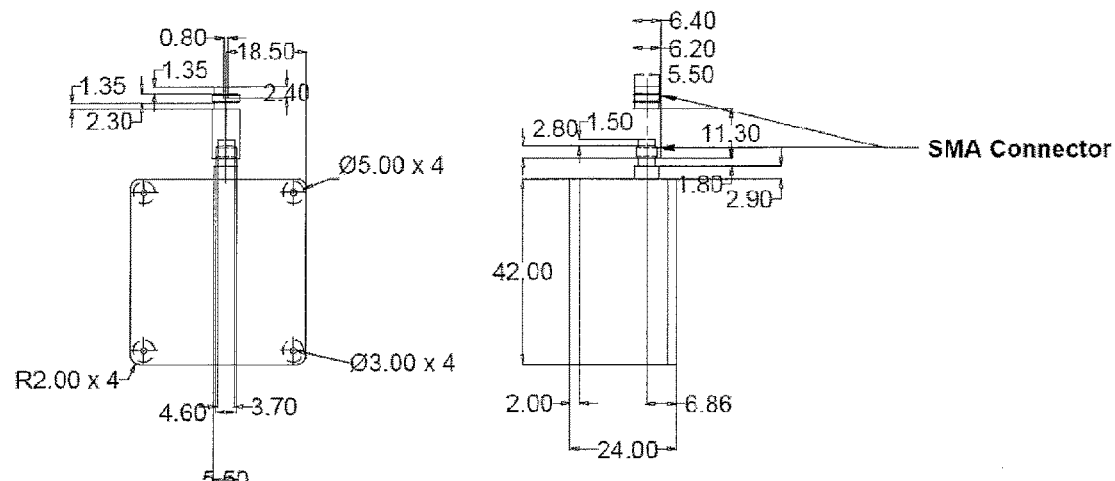
Figure 15B
Figure 15C

DEVICES AND METHODS FOR MEASURING LIGHT

CROSS-REFERENCE TO RELATED APPLICATIONS

This application claims priority to U.S. Provisional Application Nos. 61/698,995, filed Sep. 10, 2012, and 61/784,827, filed Mar. 14, 2013, each of which is hereby incorporated by reference.

FIELD OF THE INVENTION

The invention relates to devices and methods for collecting and measuring light.

BACKGROUND OF THE INVENTION

Bench-top integrating spheres are considered the most accurate and reliable devices to collect and subsequently measure light. These spheres, however, are relatively large and are not disposed to portability. Other devices, e.g., cosine correctors, become ineffective as their size increases, rendering them not viable for certain applications. This leads to a lack of portable and accurate light collecting and measuring devices.

The American Conference of Governmental Industrial Hygienists publishes recommended maximum daily exposure levels to blue light and UV light. Most manufacturers of dental curing resins supply protective eyewear, but it has been reported that there is a wide range in the effectiveness of this protective eyewear. Current commonly used protective glasses/shields may prove inadequate as the radiation intensity of light curing units ("LCUs") further increases. Lack of eye protection may also occur if a filter is used to protect against emission from a lamp with properties other than the lamp for which the filter has been intended.

There is a need in the art to develop a portable device that can quickly collect and measure light from an external source, e.g., for accurately measuring the performance of the wide range of dental LCUs, which are currently being used in dental clinics globally. This type of testing could then be used to ensure that 1) the LCU being used is appropriate for the resin composite materials being cured; 2) the LCU's energy output is optimized with the time used to ensure that sufficient energy is being delivered to cure the resin materials being used; and 3) the LCU is functioning properly, is not damaged, and/or the light output is not obstructed by resin or other light obstructing material. In addition, there is a need in the art for a light collecting and measuring device that can quickly evaluate the effectiveness of protective eyewear and/or protective shields used with LCUs in dental clinics.

SUMMARY OF THE INVENTION

The devices and methods of the present invention satisfy the need in the art described above. The invention features a device that includes: a) a light diffusing element that includes: i) an element including a top portion, a bottom portion, and a side portion, where the top portion includes a screen, the bottom portion includes an inner surface that is substantially hemispherical, and the side portion includes an inner surface that is substantially cylindrical, where the side portion is connected to the top portion and the bottom portion; and ii) an outlet port in the side portion, where the outlet port is substantially parallel to the top portion and is adjacent to the bottom portion, and where the outlet port is configured to receive a light conducting conduit. The device may further include b) a light measuring component including an opening configured to receive the light conducting conduit; and c) the light conducting conduit including a first end and a second end, where the first end is optically connected to the outlet port of the light diffusing element, and the second end is optically connected to the opening in the light measuring component. In one embodiment, the light diffusing element may be enclosed within an external shell including an inner wall and an outer wall and further includes a connecting element aligned with the outlet port and further aligned with the first end of the light conducting conduit. In other embodiments, the inner surface of the side portion of the light diffusing element may be separated from the inner wall of the external shell by between 1 mm and 15 mm (e.g., 1 mm, 2 mm, 3 mm, 4 mm, 5 mm, 6 mm, 7 mm, 8 mm, 9 mm, 10 mm, 11 mm, 13 mm, and 15 mm). In yet another embodiment, the inner surface of the side portion of the light diffusing element may be separated from the inner wall of the external shell by a distance that is sufficient to prevent light from penetrating the inner surface of the side portion or the bottom portion of the light diffusing element and interacting with the inner wall of the external shell, e.g., separated by the thickness of the material used to construct the light diffusing element.

In any of the above embodiments, the element allows for substantially uniform light diffusion across the inner surfaces. The inner surfaces include, e.g., polytetrafluoroethylene (e.g., Teflon® or Spectralon® from Labsphere Inc.), polyoxymethylene (e.g., Delrin®), barium sulfate (e.g., 6080 White Reflectance Coating from Labsphere Inc.) or other Lambertian coating (e.g., Spectraflect® or Duraflect® from Labsphere Inc.). The remainder of the light diffusing element may include a solid material, e.g., plastic, ceramic, glass, or metal (e.g., brass).

In any of the above embodiments, the top portion may further include an aperture having a diameter substantially equivalent to or smaller than the diameter of the substantially cylindrical inner surface of the side portion, where the screen covers the aperture. In other embodiments, the top portion of the light diffusing element may include a solid material, e.g., plastic, ceramic, glass, or metal (e.g., brass).

In any of the above embodiments, the external shell may include a solid material, e.g., plastic, ceramic, glass, or metal (e.g., brass).

In any of the above embodiments, the screen may be substantially square, circular, or disc-shaped and may be sized to cover the side portion of the light diffusing element. In particular embodiments the screen may be a disc having dimensions of about 28 mm in diameter (e.g., 10 mm, 15 mm, 20 mm, 25 mm, 30 mm, 35 mm, or 40 mm in diameter) and is between 0.1 mm and 5 mm thick (e.g., 0.1 mm, 0.5 mm, 1 mm, 2 mm, 3 mm, or 5 mm thick).

In some embodiments, the screen includes polytetrafluoroethylene (e.g., Teflon® or Spectralon® from Labsphere Inc.), polyoxymethylene (e.g., Delrin®), barium sulfate (e.g., 6080 White Reflectance Coating from Labsphere Inc.) or other Lambertian coating (e.g., Spectraflect® or Duraflect® from Labsphere Inc.). In other embodiments, the screen may include a transparent or other translucent material. In yet other embodiments, the screen may be coated with a translucent Lambertian coating. In further embodiments, the screen may further include a one-way mirror, where the one-way mirror allows light into the light diffusing element but substantially blocks light from exiting the light diffusing element through the one-way mirror.

In any of the above embodiments, the device may further include a filter above or below the screen. In one embodiment, the filter above the screen may cover the aperture of the top portion. In any of the above embodiments, the filter may be selected from a group consisting of glass, a neutral density filter, a band pass filter, and a blue band pass filter. In any of the above embodiments, the filter may filter wavelengths greater than 500 nm (e.g., 510 nm, 550 nm, 600 nm, 700 nm, or 800 nm). The filter may also physically protect the screen from damage, i.e., be located on top of or external to the screen.

In any of the above embodiments, the height of the substantially cylindrical inner surface of the side portion may be between 1 mm and 50 mm (e.g., 1 mm, 2 mm, 5 mm, 10 mm, 15 mm, 20 mm, 25 mm, 30 mm, 35 mm, 40 mm, 45 mm, and 55 mm).

In some embodiments, the aperture in the top portion of the light diffusing element may have a diameter between 4 mm and 30 mm (e.g., 4 mm, 5 mm, 8 mm, 10 mm, 15 mm, 20 mm, 25 mm, and 30 mm). In other embodiments, the aperture in the top portion of the light diffusing element may have a diameter between 30 mm and 300 mm (e.g., 30 mm, 50 mm, 90 mm, 100 mm, 150 mm, 200 mm, 250 mm, and 300 mm). In a specific embodiment, the diameter of the aperture is about 16 mm.

In any of the above embodiments, the light conducting conduit may have an inner diameter between 10 µm and 1000 µm (e.g., 10 µm, 20 µm, 50 µm, 100 µm, 300 µm, 500 µm, 700 µm, and 1000 µm in diameter). In some embodiments, the light conducting conduit may have a length between 1 mm and 300 mm (e.g., 1 mm, 10 mm, 50 mm, 75 mm, 100 mm, 150 mm, 200 mm, 250 mm, and 300 mm in length).

In any of the above embodiments, the opening of the light measuring component may be between 10 µm and 1000 µm in diameter (e.g., 10 µm, 20 µm, 50 µm, 100 µm, 300 µm, 500 µm, 700 µm, and 1000 µm in diameter). In further embodiments, the light measuring component is capable of measuring between 150 nm and 1000 nm wavelengths (e.g., 150 nm, 200 nm, 300 nm, 400 nm, 500 nm, 600 nm, 700 nm, 800 nm, 900 nm, and 1000 nm wavelengths). In some embodiments, the light measuring component is capable of measuring between 360 nm and 540 nm wavelengths (e.g., 360 nm, 400 nm, 420 nm, 440 nm, 480 nm, 500 nm, 520 nm, and 540 nm wavelengths).

In any of the above embodiments, the device further includes an external housing enclosing the light diffusing element, the light measuring component, and the light conducting conduit. In one embodiment, the external housing may further include a window aligned with the screen of the top portion of the light diffusing element. In another embodiment, the external housing may further include an opening adjacent to the light measuring component, where the opening is configured to receive a cable.

In any of the above embodiments, the device may further include a processor to which data collected by the light measuring component is communicated for analysis.

In any of the above embodiments, the device may further include a display that is capable of displaying an indicator.

The invention further features a method for measuring light, including directing light from a light source into the light diffusing element of a device of the invention, where: a) the light entering the light diffusing element diffuses within the light diffusing element; b) a portion of the light diffused within the light diffusing element exits the light diffusing element through the outlet port and is transported through the light conducting conduit to the light measuring component; c) the light measuring component measures properties of the light delivered from the light conducting conduit to produce data and communicates the data to a processor; and d) the processor analyzes the data and generates an indicator.

In some embodiments of the method, the light measuring component may measure visible light, infrared light, or UV light. In other embodiments, the method may further include use of a light blocking material, and where in step (a) light from the light source passes through the light blocking material and enters the light diffusing element. In any of the above embodiments of the method of the invention, the light source may be capable of curing dental resin. In one embodiment, the light blocking material may be a shield or pair of glasses that protect against ocular damage from light generated by dental resin curing tools. In other embodiments, the indicator may be power, irradiance, or maximum exposure time.

The method of the invention may further include a calibration step including: e) providing a pre-calibrated lamp; f) generating a light beam from the pre-calibrated lamp and directing the light beam into the light diffusing element; g) obtaining an indicator value and comparing the value to an indicator value associated with the pre-calibrated lamp; h) determining a correction factor based on the comparison made in step (g) above; and i) applying the correction factor obtained in step (h) above in to generate the indicator in step (d) above.

As used herein, the term "light diffusing element" refers to a component in which light may enter and diffuse.

As used herein, the term "light collector" refers to a device that includes a light diffusing element and an external shell.

As used herein, the terms "top portion," "bottom portion," and "side portion" refers to distinct portions of a light diffusing element and do not necessarily describe absolute spatial positions.

As used herein, the term "outlet port" refers to an opening or gap through which light may travel.

As used herein, the term "about" refers to within 10% of the recited value. All distances, percentages, and measurements recited herein may be modified by the term "about."

As used herein, the term "Lambertian" refers to a diffusely reflecting surface.

As used herein, the term "screen" refers to an object that is white, translucent, and Lambertian, e.g., a solid layer made from or coated with polytetrafluoroethylene (e.g., Teflon® or Spectralon® from Labsphere Inc.), polyoxymethylene (e.g., Delrin®), barium sulfate (e.g., 6080 White Reflectance Coating from Labsphere Inc.) or other Lambertian coating (e.g., Spectraflect® or Duraflect® from Labsphere Inc.).

As used herein, the term "adjacent" refers to a location within 10 mm of a reference point, e.g., within 9 mm, 8 mm, 7 mm, 6 mm, 5 mm, 4 mm, 3 mm, 2 mm, or even 1 mm.

As used herein, the term "opening" refers to a gap in material, e.g., a slit, an entrance slit, or a narrow aperture.

As used herein, the term "connector" refers to an object that joins two separate objects.

As used herein, the term "light measuring component" refers to a device that is capable of analyzing the spectral components and/or intensity of light and producing an electronic signal (either analog or digital), e.g., a spectrometer, or a light meter, or a photometer or a photodiode or a photomultiplier tube, or a CCD array, or a CMOS sensor or a photovoltaic device.

As used herein, the term "light conducting conduit" refers to an enclosed path, e.g., a channel, tube, or trough that is capable of transmitting light, e.g., a fiber optic cable or liquid light guide.

As used herein, the terms "communicates" and "communicated" refer to the act of transferring electronic signals (digital or analog), e.g., via wireless communication, via a USB cable, or through internal circuitry.

As used herein, the term "light blocking material" refers to a material that prevents or reduces the passage of light, e.g., visible light or UV light.

As used herein, the term "indicator" refers to a representation of data, e.g., maximum exposure time, transmitted spectral power, transmitted light power, or transmitted light intensity.

BRIEF DESCRIPTION OF THE DRAWINGS

FIG. 5A is a schematic diagram of a top view of the top portion of a light diffusing element.

FIG. 5B is a schematic diagram of a side view of the top portion of a light diffusing element.

FIG. 15A-15C are a set of schematic diagrams of a spectrometer. Units are in millimeters.

FIG. 17A shows various views of the external housing. FIG. 17B shows various cross-sectional and exploded views of the external housing, light diffusing element, and light measuring component. FIG. 17C shows a cross-sectional view of the fastening of the top and bottom of the external housing (not to scale). FIG. 17D shows the light diffusing element, light conducting conduit, and light measuring component placed in the bottom of the external housing. FIG. 17E shows various views of the bottom of the external housing. FIG. 17F shows various views of the top of the external housing. FIG. 17G shows various views of a rubber gasket for moisture protection around a USB port. FIG. 17H shows various views of a spacer that provides an optional distance aid between the light diffusing element and the light conducting conduit. FIG. 17I shows various views of the light diffusing element. FIG. 17J shows various views of the light conducting conduit. FIG. 17K shows various views of an exemplary light measuring component. FIG. 17L shows various views of the screen. Units are in millimeters.

DETAILED DESCRIPTION

Figure 1:
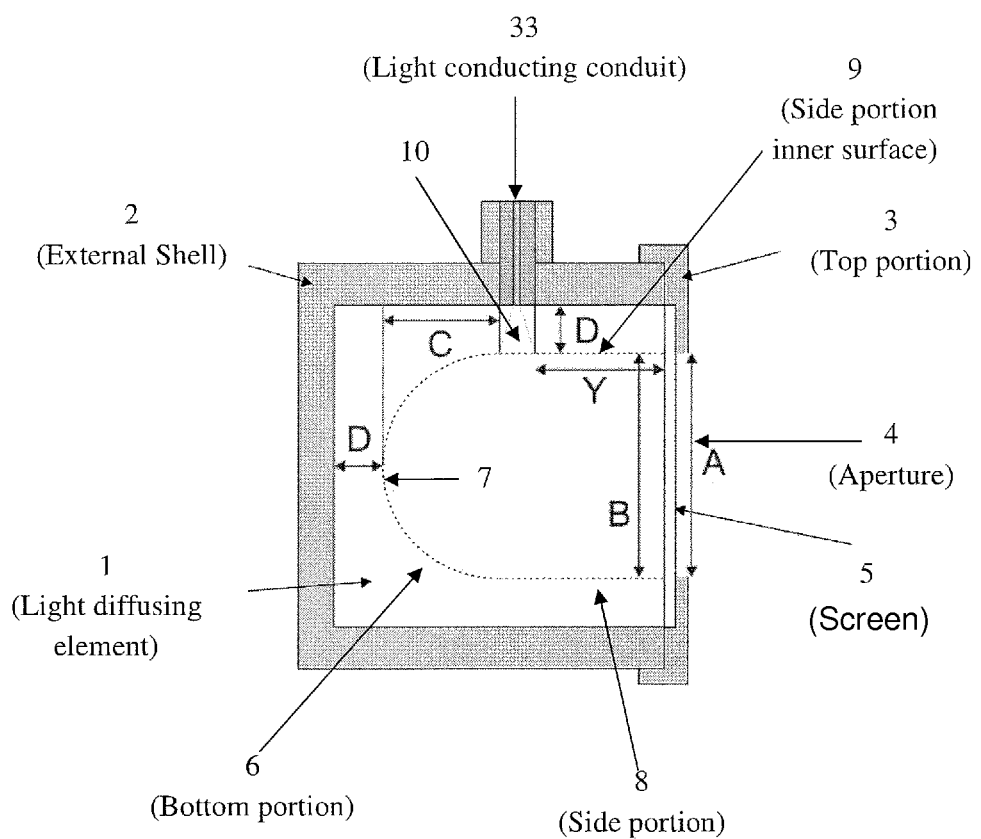
FIG. 1 is a schematic diagram of a light collector.

The invention features devices and methods for collecting and measuring light from external light sources. In general, the devices of the invention feature a light diffusing element, e.g., as part of a light collector, connected by a light conducting conduit, e.g., a fiber optic cable, to a light measuring component, e.g., a spectrometer. The light diffusing element allows for substantially uniform light diffusion across its surface and accurate measurements, while permitting the total footprint of the device to remain relatively small and portable. The light diffusing element also allows flexibility in scaling of the device to permit use in a wide range of applications.

The devices of the invention may be employed in different configurations. In the simplest configuration, the device includes a light diffusing element that includes top portion (3) that includes screen (5) and an optional aperture (4); bottom portion (6), which includes bottom portion inner surface (7) that is substantially hemispherical; and side portion (8), which includes side portion inner surface (9) that is substantially cylindrical. Side portion (8) further includes outlet port (10). The light diffusing element may or may not be enclosed within an external shell (2) to form a light collector. An exemplary light diffusing element in a light collector is shown in FIGS. 1 and 2A-2C.

Referring to FIG. 1, the diameter of aperture (4), dimension (A), may be equivalent to or smaller than the diameter of bottom portion inner surface (7), distance (B). Dimensions (A) and/or (B) may vary, e.g., between 4 mm and 500 mm, e.g., between 10 mm and 15 mm, between 8 mm and 30 mm, between 4 mm and 30 mm, between 20 mm and 25 mm, or between 30 mm and 300 mm. In some embodiments, dimensions (A) and/or (B) are about 15 mm. In some embodiments, dimensions (A) and/or (B) are, e.g., 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 110, 120, 130, 140, 150, 160, 170, 180, 190, 200, 210, 220, 230, 240, 250, 260, 270, 280, 290, or 300 mm, or may be between any two of these values. In some embodiments, dimension A is, e.g., 100%, 95%, 90%, 85%, 80%, 75%, 70%, 65%, 60%, 55%, 50%, or less than 50% of dimension B.

The distance between a plane tangent to the base of bottom portion inner surface (7) and the bottom of outlet port (10), dimension (C), may be about half of dimension (B), or 30%, 35%, 40%, 45%, 50%, 55%, 60%, 65%, or 70% of dimension (B), or may be between any two of these values. The distance between bottom portion inner surface (7) and the internal wall of external shell (2), and/or the distance between side portion inner surface (9) and the internal wall of external shell (2), dimension (D), may vary in accordance with the material and application of the device. In some embodiments, dimension (D) is sufficient to prevent light from penetrating through light diffusing element (1) and interacting with the internal surface of external shell (2), e.g., by the thickness of the material used to manufacture the side and bottom portions. Dimension (D) may be between 1 mm and 100 mm, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, or 100 mm, or may be between any two of these values. In some embodiments, dimension (D) is about 3 mm or greater. The distance from the bottom of screen (5) to the top of outlet port (10), dimension (Y), may be between 1 mm and 100 mm, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, or 100 mm, or may be between any two of these values. In some embodiments, dimension (Y) may be between 10% and 300% of dimension (C), e.g., 10%, 20%, 30%, 40%, 50%, 60%, 70%, 80%, 90%, 100%, 110%, 120%, 130%, 140%, 150%, 160%, 170%, 180%, 190%, 200%, 225%, 250%, 275%, or 300% of C, or may be between any two of these values. In some embodiments, dimension (Y) is about 50%, 100%, or 200% of dimension (C).

The geometrical configuration of light diffusing element (1) permits accurate measurement and collection of light independent of the angle at which the light enters the element and/or device.

The side, bottom, and top portions may be manufactured from any suitable material, e.g., polytetrafluoroethylene (e.g., Teflon® or Spectralon® from Labsphere Inc.), polyoxymethylene (e.g., Delrin®), barium sulfate (e.g., 6080 White Reflectance Coating from Labsphere Inc.) or other Lambertian coating (e.g., Spectraflect® or Duraflect® from Labsphere Inc.). These portions may also include other materials, e.g., plastic, ceramic, glass, or metal, on which Lambertian materials are layered or coated. When the top portion includes an aperture, the portions of the top not including the screen may be made from any material suitable to hold the screen, e.g., plastic, ceramic, glass, or metal.

The exterior shape of optional external shell (2) may be substantially cubical, cylindrical, pyramidal, or a rectangular solid. The internal surface and cavity shape of external shell (2) may vary according to the external shape of the light diffusing element, e.g., it may conform to the exterior shape.

In the descriptions that follow, in some instances, numbered elements not shown in a referenced figure are shown in one or more preceding figures.

Figure 2A:
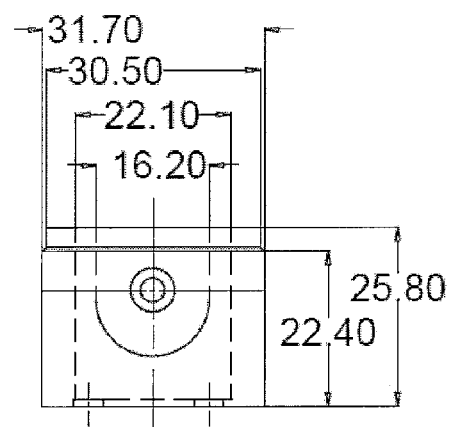
FIG. 2A is a schematic diagram of the front view of a light collector. Units are in millimeters.
Figure 2B:
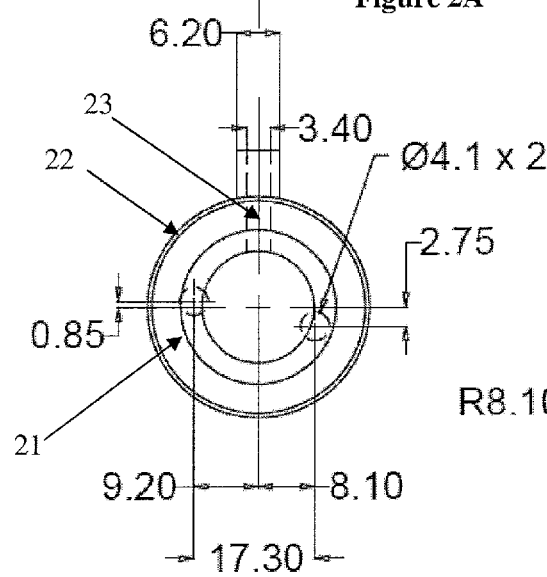
FIG. 2B is a schematic diagram of the top view of a light collector. Units are in millimeters.
Figure 2C:
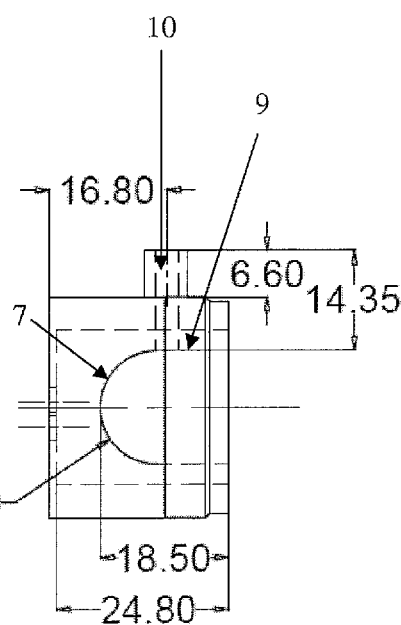
FIG. 2C is a schematic diagram of the cross-sectional view of a light collector showing the light diffusing element. Units are in millimeters. In some embodiments, the connection point of the light conducting conduit does not scale with the other dimensions of the light collector if made bigger.

Referring to FIGS. 2A-2C, a front view, a top view, and a cross-sectional view, showing the light diffusing element and external shell in the light collector are shown. This shell may include external shell inner surface (21), external shell outer surface (22), and cavity (23) to fit a connection element. External shell (2) may be made of any solid material, e.g., plastic, ceramic, glass, or metal. Outlet port (10) passes through both the external surface of the light diffusing element and side portion inner surface (9) of the light diffusing chamber defined by bottom portion inner surface (7) and side portion inner surface (9). Outlet port (10) may be located adjacent to cavity (23) of external shell (2) so as to create a channel from the inner surface of the light diffusing chamber to the outer surface of the external shell.

In other embodiments, the light diffusing element is connected to a light measuring device by a light conducting conduit. This device may or may not be enclosed in an external housing (34). The device may also include connectors to external processors or computers as are known in the art, e.g., USB and Ethernet. Alternatively, the device may include hardware for wireless transmission of data. The device may also include a processor or computer within it to analyze data and/or provide an indicator. When an external housing is employed, the light diffusing element may or may not be enclosed in an external shell (2).

Figure 3:
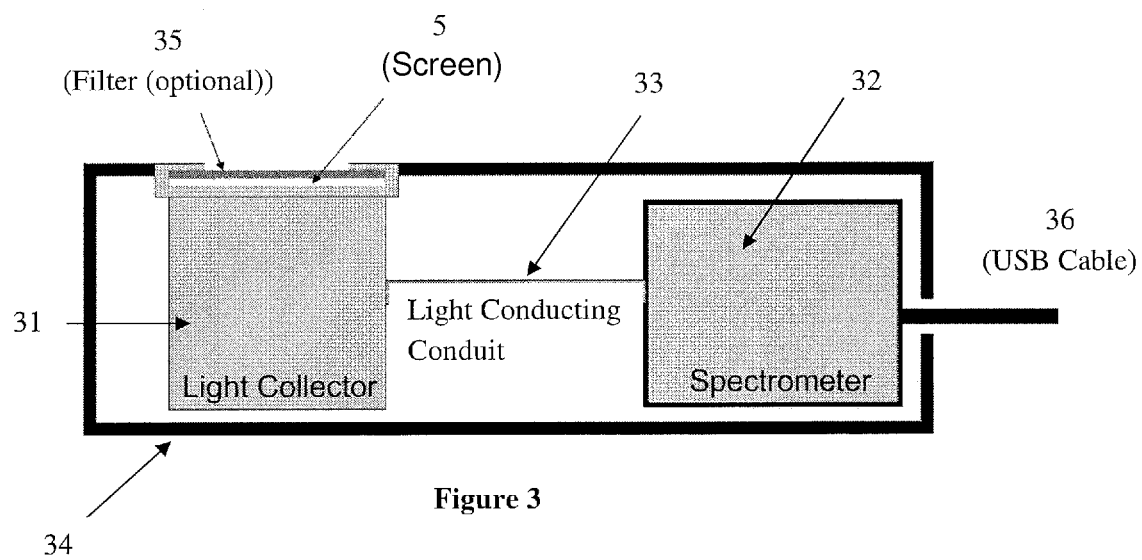
FIG. 3 is a schematic diagram of a light collector, light conducting conduit, and spectrometer. Also depicted are an aperture screen, an optional filter, and a USB cable capable of connecting, e.g., to a laptop.

Referring to FIG. 3, light collector (31), which includes light diffusing element (1) enclosed in external shell (2), is connected to light measuring element (32), e.g., a spectrometer, via light conducting conduit (33). At the top of light collector (31) are screen (5) and optional filter (35). USB cable (36) optionally connects spectrometer (32) to an external computer, e.g., a laptop.

The surface of screen (5), e.g., the material of the surface or a coating applied to the surface, is white, translucent, and Lambertian, e.g., made from or coated with polytetrafluoroethylene (e.g., Teflon® or Spectralon® from Labsphere Inc.), polyoxymethylene (e.g., Delrin®), barium sulfate (e.g., 6080 White Reflectance Coating from Labsphere Inc.) or other Lambertian coating (e.g., Spectraflect® or Duraflect® from Labsphere Inc.). Screen (5) is located above the side and bottom portions of light diffusing element (1) of light collector (31). When the top includes an aperture (4), the screen may be sized to cover at least aperture (4) of light diffusing element (1). The length of screen (5) may be equal to or greater than the diameter of the substantially hemispherical bottom portion. In some embodiments, the device may include a filter, e.g., glass (such as alkali-aluminosilicate sheet toughened glass (Gorilla® glass)), neutral density filter, blue band filter, or a filter that filters wavelengths of at least 500 nm. Filter (35) may be located in the top portion of light diffusing element (1) above or below aperture screen (5). In certain embodiments, the filter acts as a physical barrier to protect the screen from damage. When an aperture (4) is present in the top portion, it may include one or more tiered recesses into which the screen (5) and any filter (35) rest. The tiered recesses provide physical support for the perimeter of the screen and filter. Alternative ways of attaching a screen and/or filter are known. For example, the screen may be part of a component that screws or clamps to the side and bottom portions. The screen may also be a sheet of material that is compressed against the side portion, e.g., by an external housing as shown in FIGS. 17A-17L.

Referring to FIGS. 5A and 5B, FIG. 5A is a top view of top portion (3) of light diffusing element (1), and FIG. 5B is a side view of top portion (3) of light diffusing element (1). Top portion (3) includes graduated diameters and/or widths, with the base being the largest in diameter and/or width and the top level being the smallest in diameter. In certain embodiments, screen (5) and/or filter (35) are attached, e.g., affixed or screwed, to top portion (3) of light diffusing element (1). If filter (35) is used, it may be attached above or below screen (5) in top portion (3). The top portion may be attached to the rest of the device, e.g., via threads (e.g., as shown in FIGS. 5A and 5B).

Figure 4:
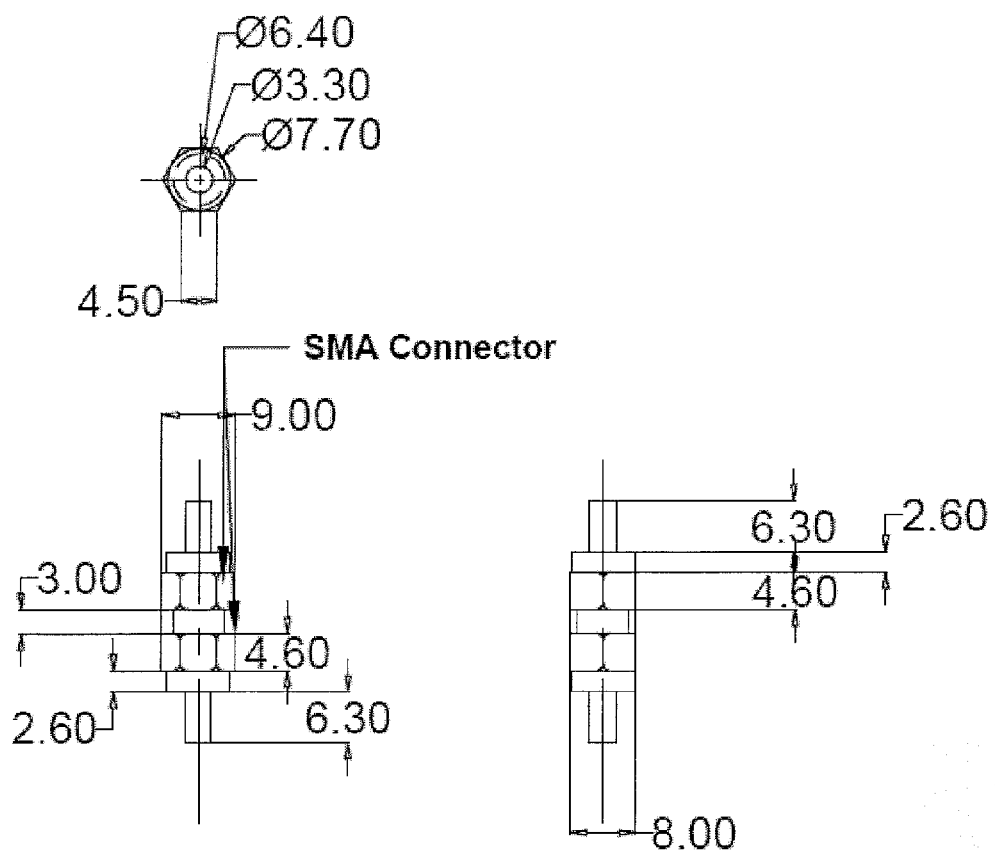
FIG. 4 is a schematic diagram of a connecting element. Units are in millimeters.

Light conducting conduit (33) may be, e.g., a fiber optic cable or liquid light conduit. Light conducting conduit (33) may be attached to light diffusing element (1) and/or external shell (2) so that light conducting conduit (33) is disposed substantially parallel to screen (5) or aperture (4) while the opening of light conducting conduit (33) is substantially perpendicular to screen (5) or aperture (4). Light conducting conduit (33) may be between 1 mm and 500 mm in length, e.g., 1, 2, 3, 4, 5, 6, 7, 8, 9, 10, 11, 12, 13, 14, 15, 16, 17, 18, 19, 20, 25, 30, 35, 40, 45, 50, 75, 100, 125, 150, 175, 200, 250, 300, 350, 400, 450, or 500 mm, or may be between any two of these values. The inner diameter of light conducting conduit (33) may be between, 50 µm and 10,000 µm, e.g., 50, 55, 60, 65, 70, 75, 80, 85, 90, 95, 100, 125, 150, 200, 250, 500, 1,000, 2,000, 3000, 4,000, 5,000, 6,000, 7,000, 8,000, 9,000, or 10,000 µm, or may be between any two of these values. The inner diameter of light conducting conduit (33) may be selected to optimize the acceptance angle for a given application and materials. Referring to FIG. 4, the acceptance angle, $\theta_{max}$, for a fiber optic cable, e.g., a step-index multimode fiber, is calculated by the indices of refraction as follows:

$$NA = n \sin \theta_{max} = \sqrt{n_f^2 - n_c^2}$$

Where n is the refractive index of the medium light is traveling before entering the fiber; $n_f$ is the refractive index of the fiber core; and $n_c$ is the refractive index of the cladding.

Referring to FIG. 4, side views of a connection element, e.g., an SMA connection element, are shown. The external diameter of the connection element may be substantially equivalent to the diameter of outlet port (10) of light diffusing element (1). In some embodiments, the external diameter of the connection element and the diameter of outlet port (10) are within 1%, 2%, 3%, 4%, 5%, 6%, 7%, 8%, 9%, or 10% of one another. The connection element may be made out of any solid material, e.g., plastic, ceramic, glass, or metal.

Figure 6A:
FIGS. 6A-C are schematic diagrams of a spectrometer, including a high density USB port, an SMA connector, and a fiber optic stub.
Figures 6B, 6C:
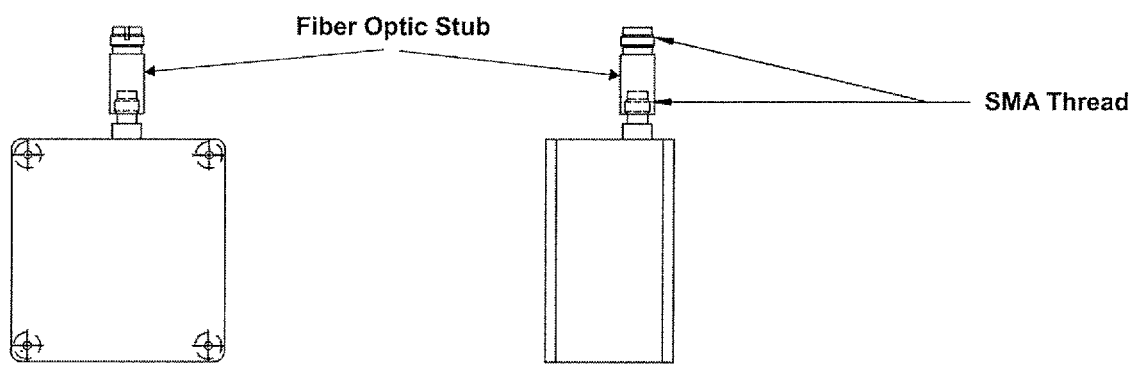

The light measuring element may be any device capable of analyzing the spectral components and/or intensity of light and encoding the information in an electronic signal, e.g., a spectrometer, a light meter, a photometer, a photodiode, a photomultiplier tube, a CCD array, a CMOS sensor, or a photovoltaic device. Spectral information may be obtained by using of appropriate filters or a diffracting or refracting element such as a grating or prism. Referring to FIGS. 6A-6C, devices of the invention may employ spectrometer (32) having slit ranges, e.g., between 1 µm and 1,500 µm, e.g., between 10 µm and 1,000 µm, between 100 µm and 500 µm, between 300 µm and 400 µm, and between 360 nm and 540 nm, e.g., 10, 20, 30, 40, 50, 60, 70, 80, 90, 100, 150, 200, 250, 300, 350, 400, 500, 600, 700, 800, 900, or 1,000 µm, or between any two of these values. Spectrometer (32) may be capable of measuring UV light, visible light, and/or infrared light. FIGS. 6B and 6C include a connector, e.g., an SMA connector, so as to facilitate connection between spectrometer (32) and light conducting conduit (33). Any connector that facilitates this connection may be used. In some embodiments of the invention, spectrometer (32) may be replaced with any light measuring component. Exemplary spectrometers are described herein, e.g., as shown in FIGS. 15A-15C.

Figure 7A:
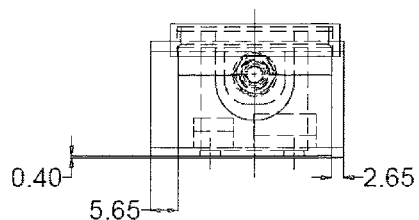
FIGS. 7A, 7B, and 7C are schematic diagrams of front, top, and side views, respectively, of a spectrometer connected to a light collector via a light conducting conduit. Units are in millimeters.
Figure 7B:
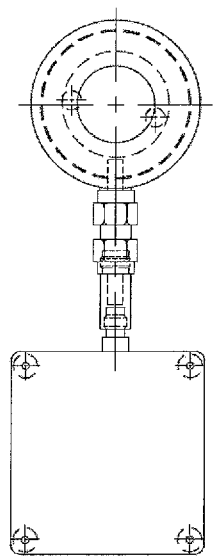
Figure 7C:
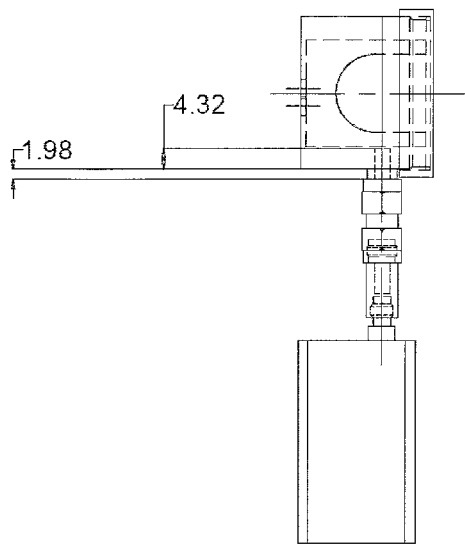
Figure 8:
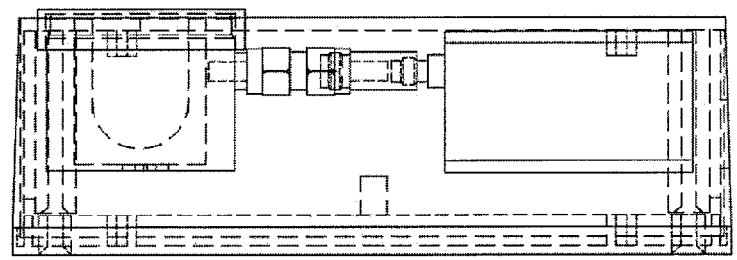
FIG. 8 is a schematic diagram depicting a side view, of the external housing and its interior with a light collector and spectrometer installed.

FIGS. 7A-7C show a light collector connected to a spectrometer, which may be placed in external housing (34). In these embodiments, a window (37) is aligned over aperture (4) and/or screen (5) of light collector (31) so as to permit light to pass through external housing (34) directly into light diffusing element (1). FIG. 8 schematically shows an exemplary assembled device.

In certain embodiments, external housing (34) may also include a port (38) in proximity to spectrometer (32) so as to allow an external processor, e.g., a computer such as a laptop computer, to connect with spectrometer (32). In these embodiments, a cable, e.g., USB cable (36), may pass through external housing (34). In still other embodiments, spectrometer (32) and/or the assembled device may further include a processor and/or display capable of and/or programmed to analyze and display the data obtained by spectrometer (32) and/or light measuring component and/or an indicator related to this data. This internal processor and/or display may generate an indicator and/or store the data.

Figure 17A:
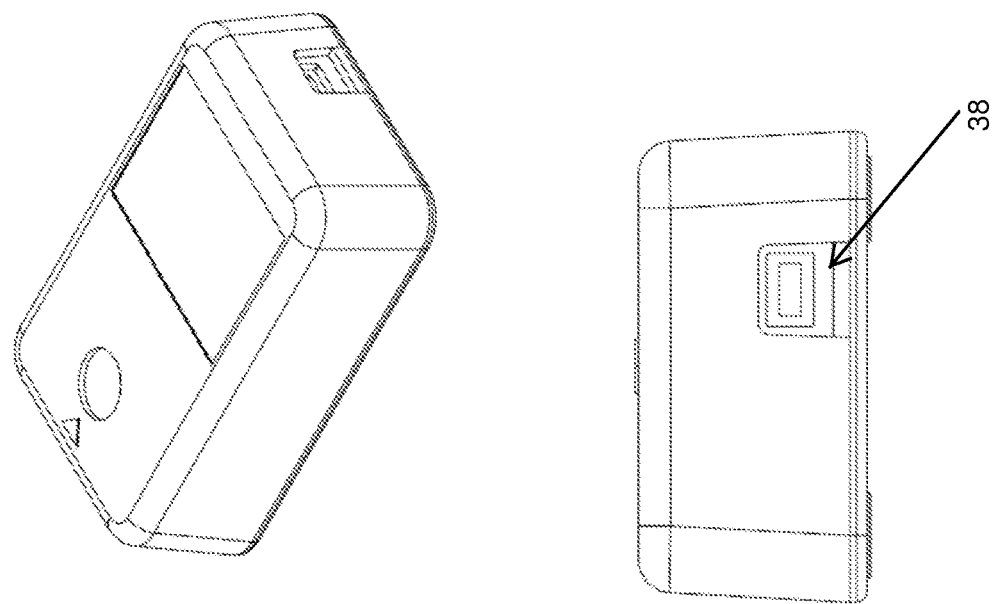
FIGS. 17A-17L are schematic diagrams of a device of the invention including a light diffusing element housed in an external housing without an external shell.
Figure 17A:
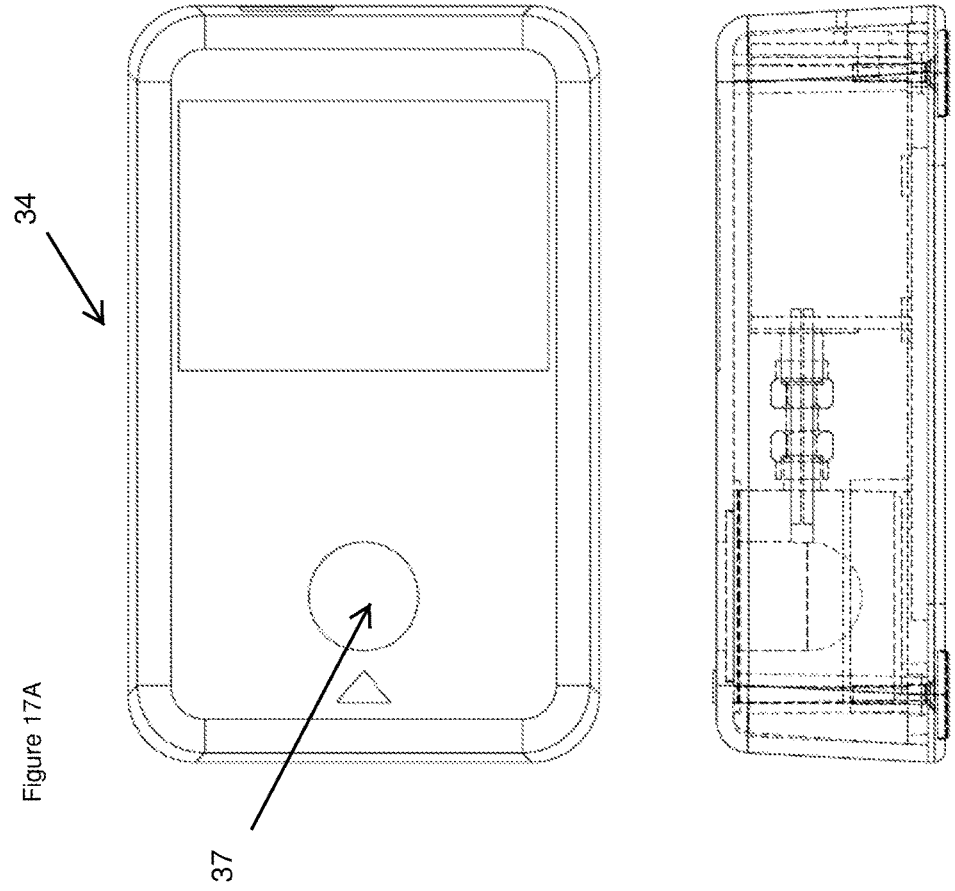
Figure 17B:
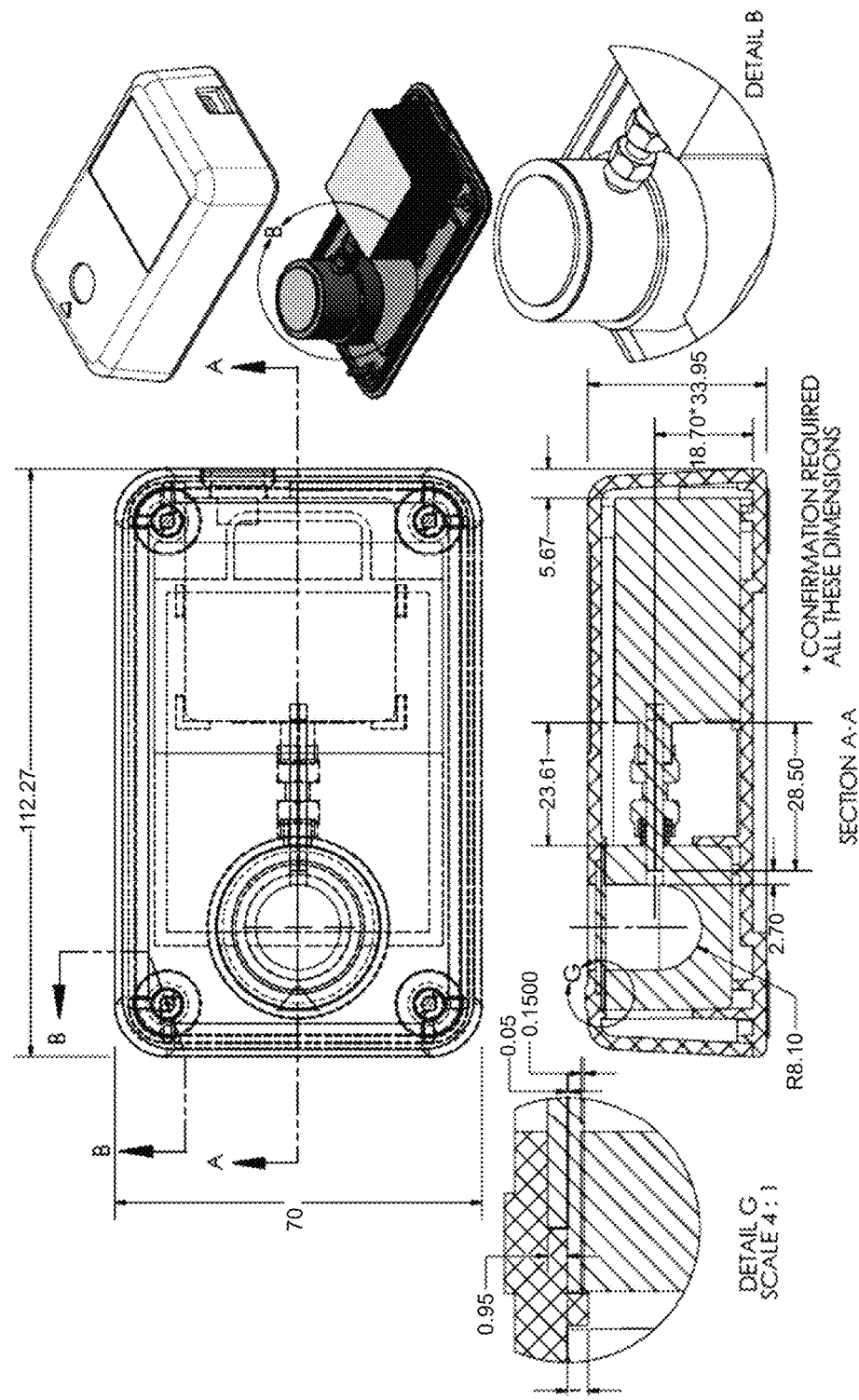
Figure 17C:
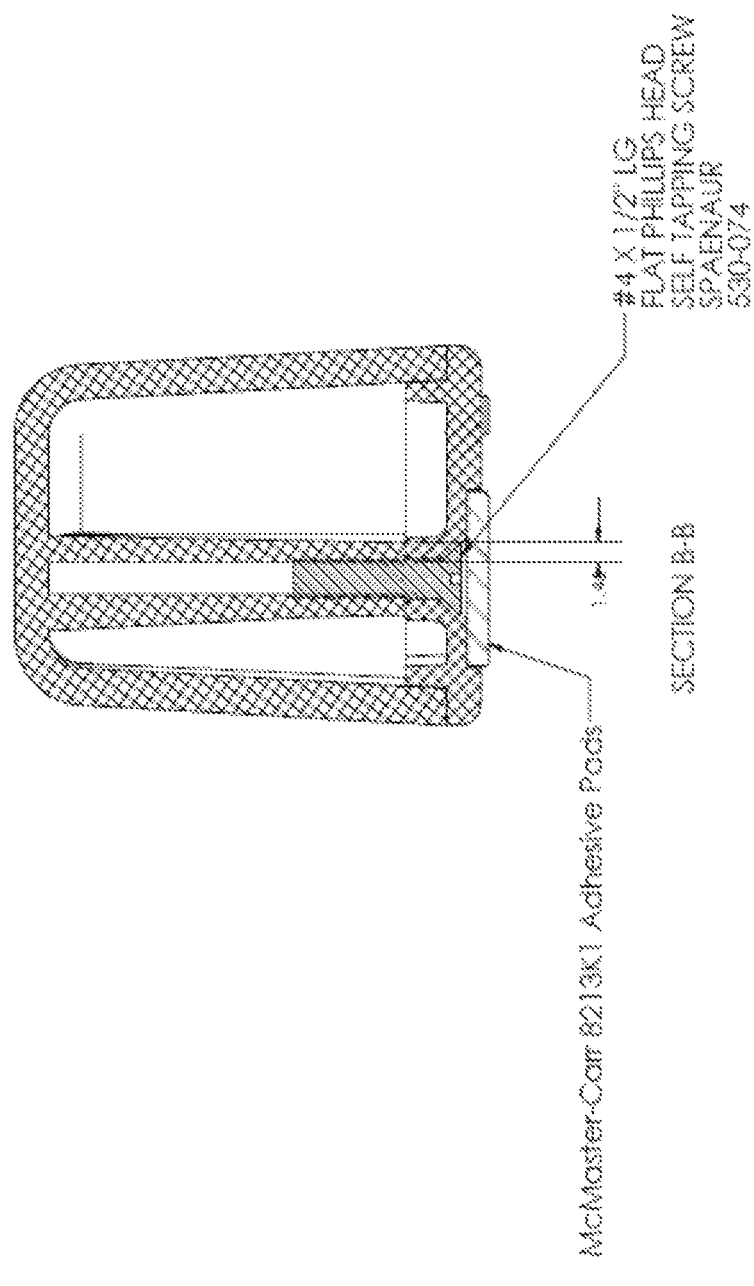
Figure 17D:
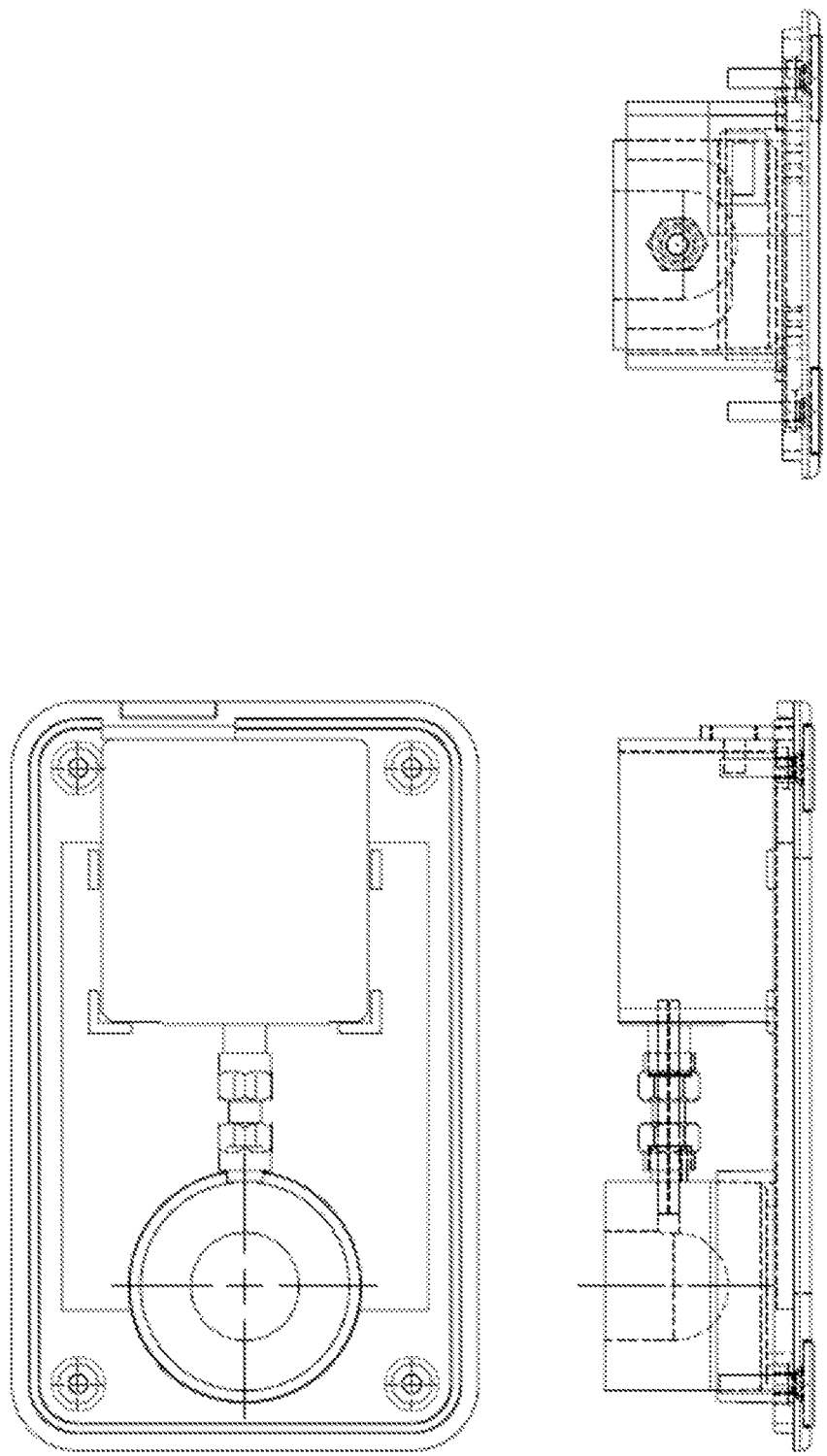
Figure 17E:
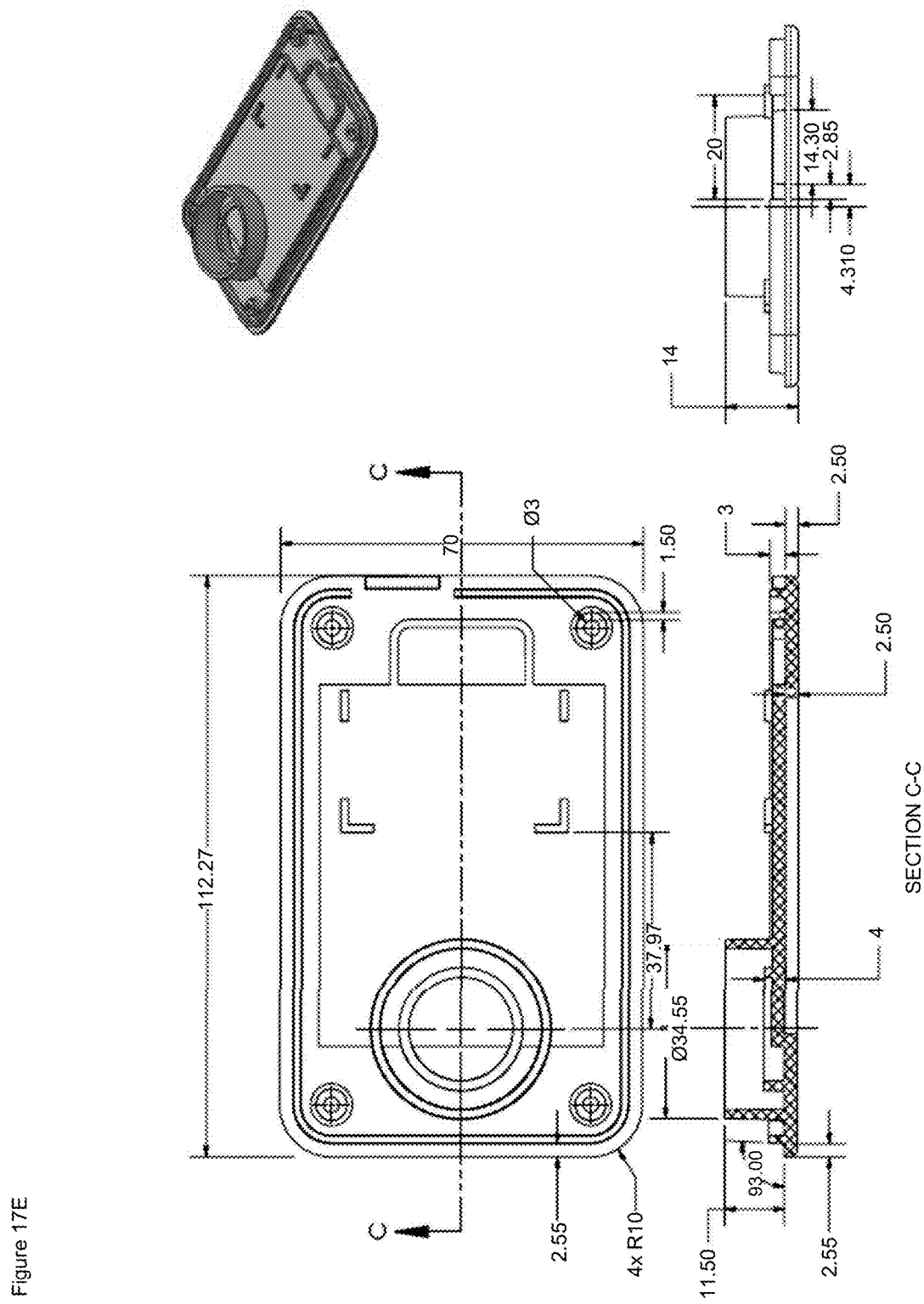
Figure 17F:
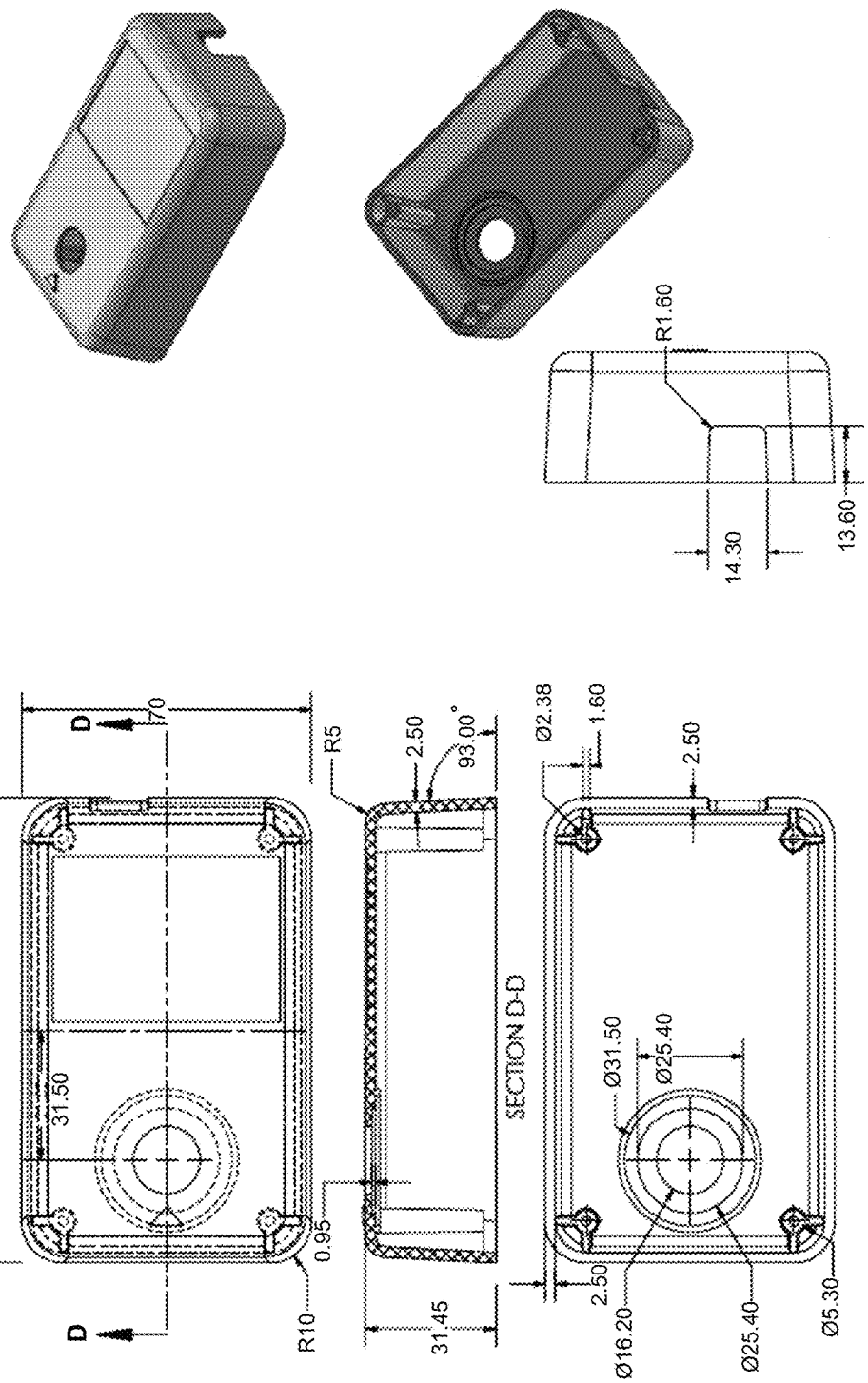
Figure 17G:
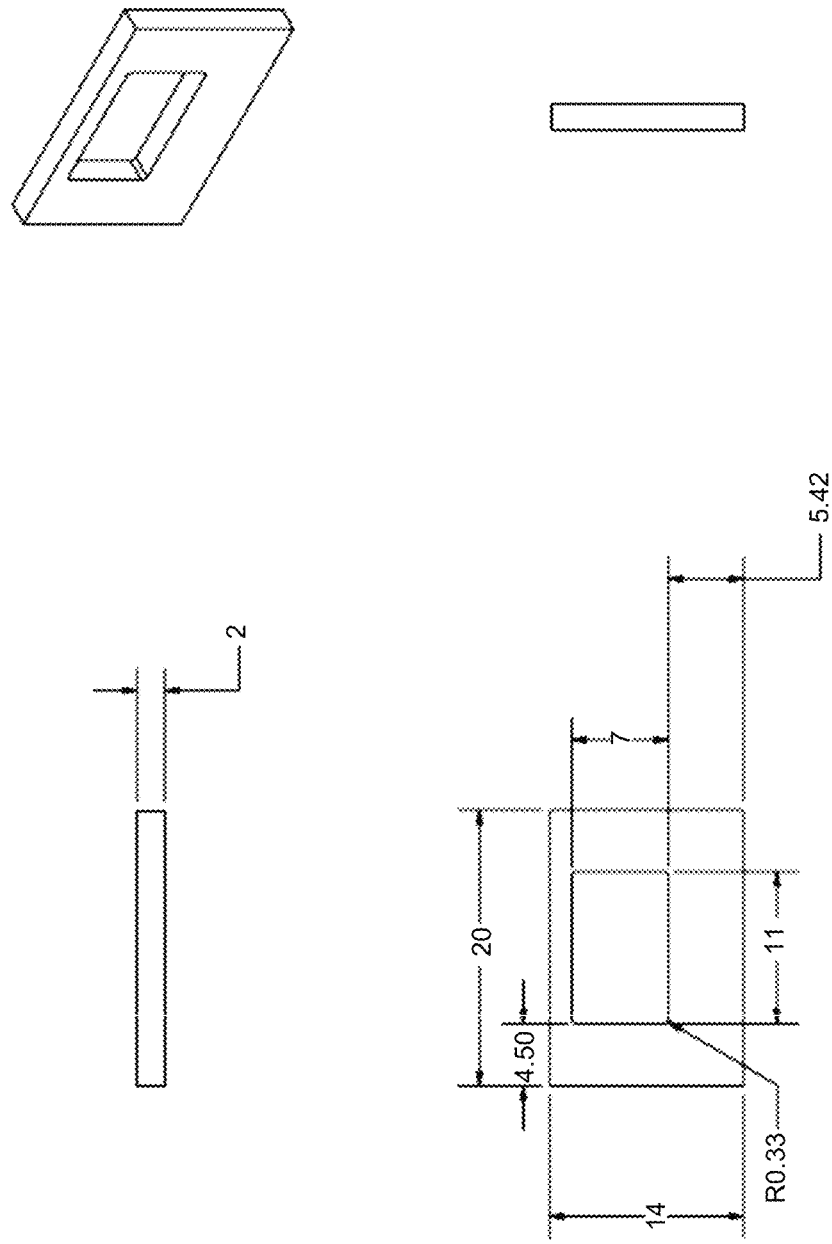
Figure 17H:
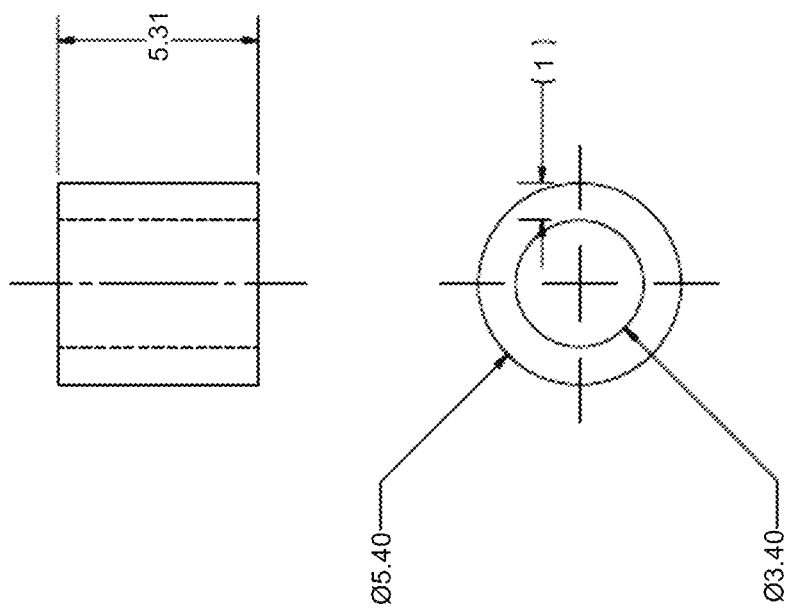
Figure 17I:
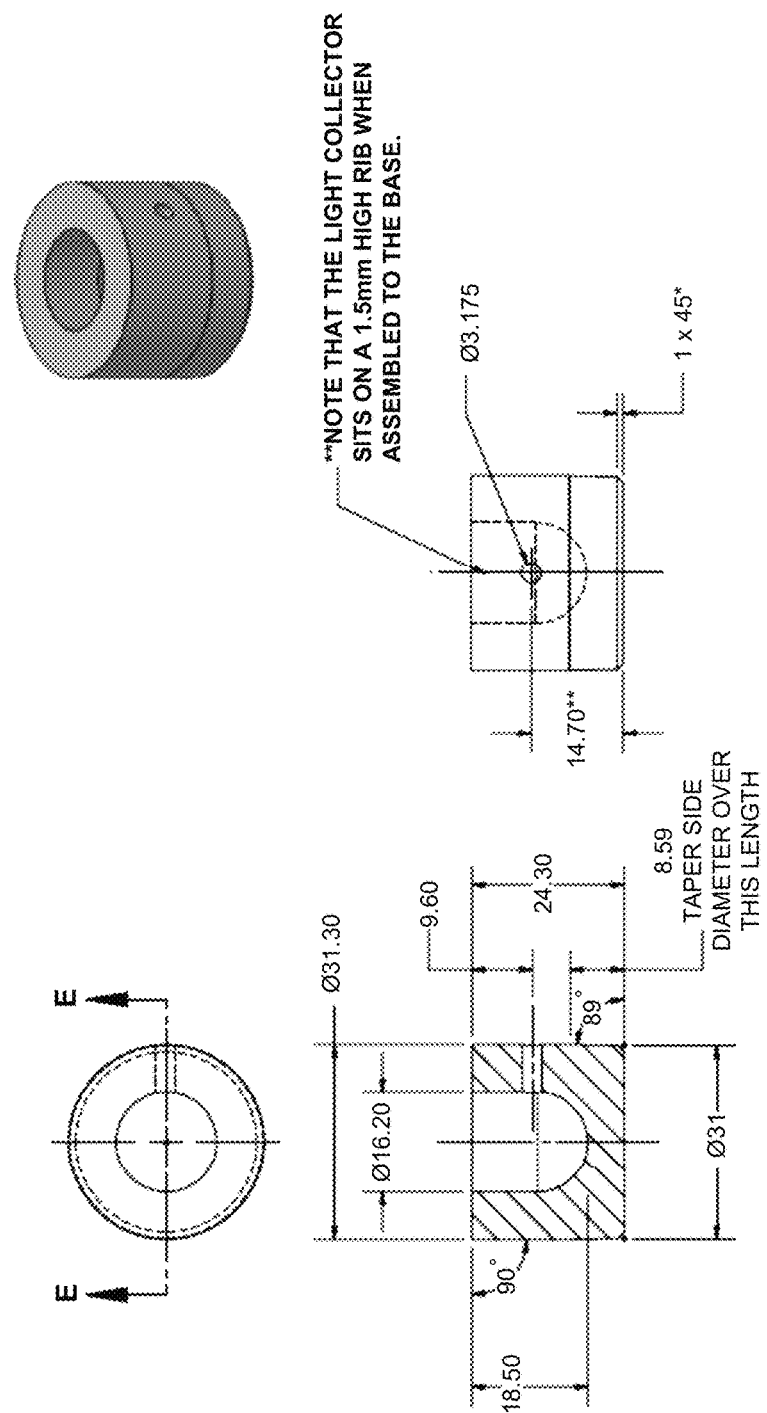
Figure 17J:
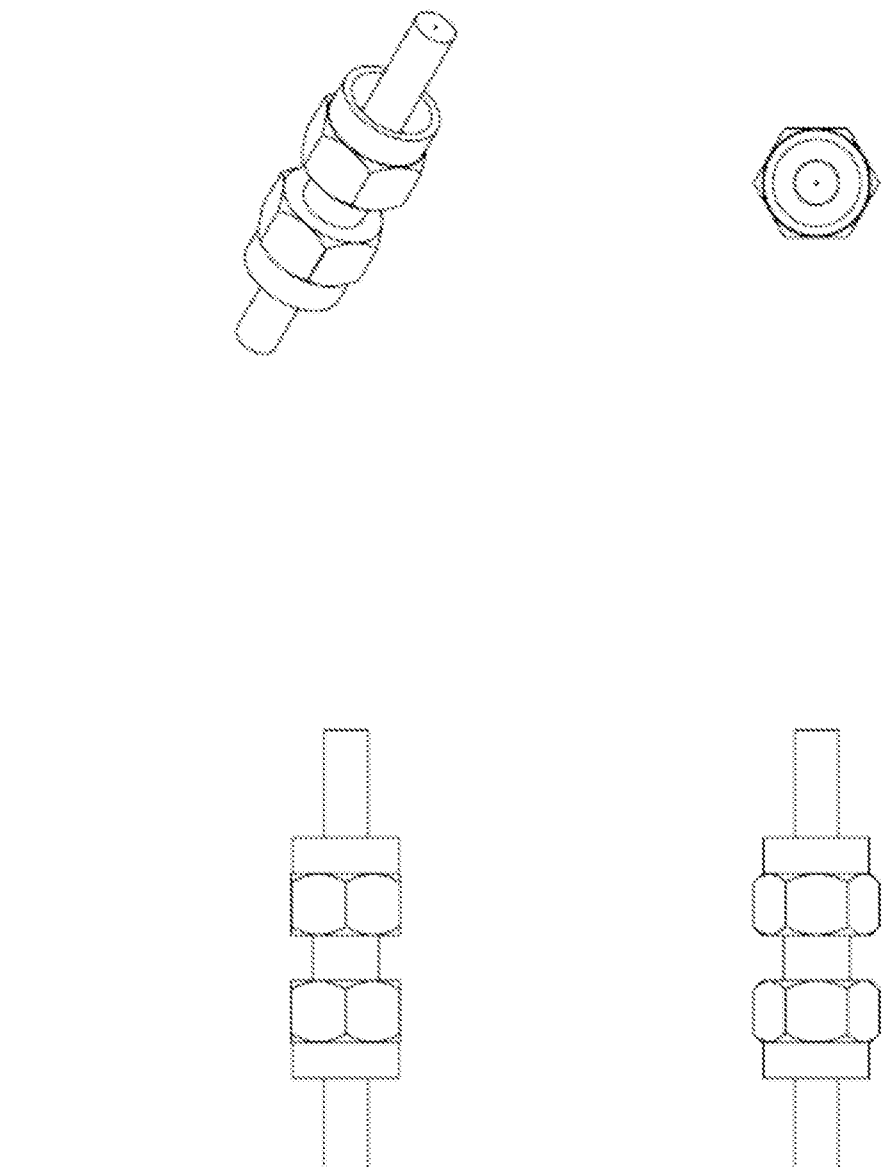
Figure 17K:
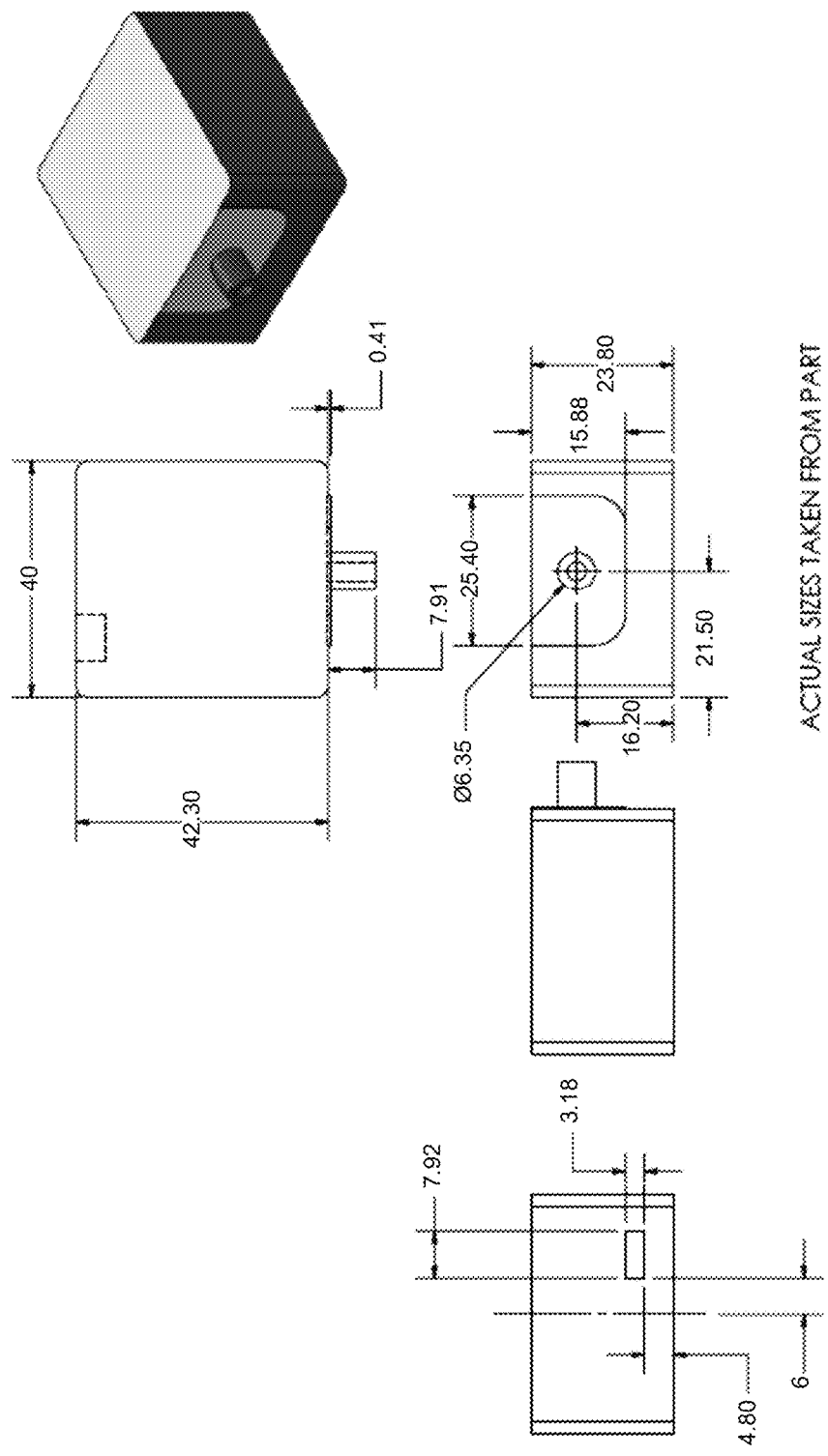
Figure 17L:
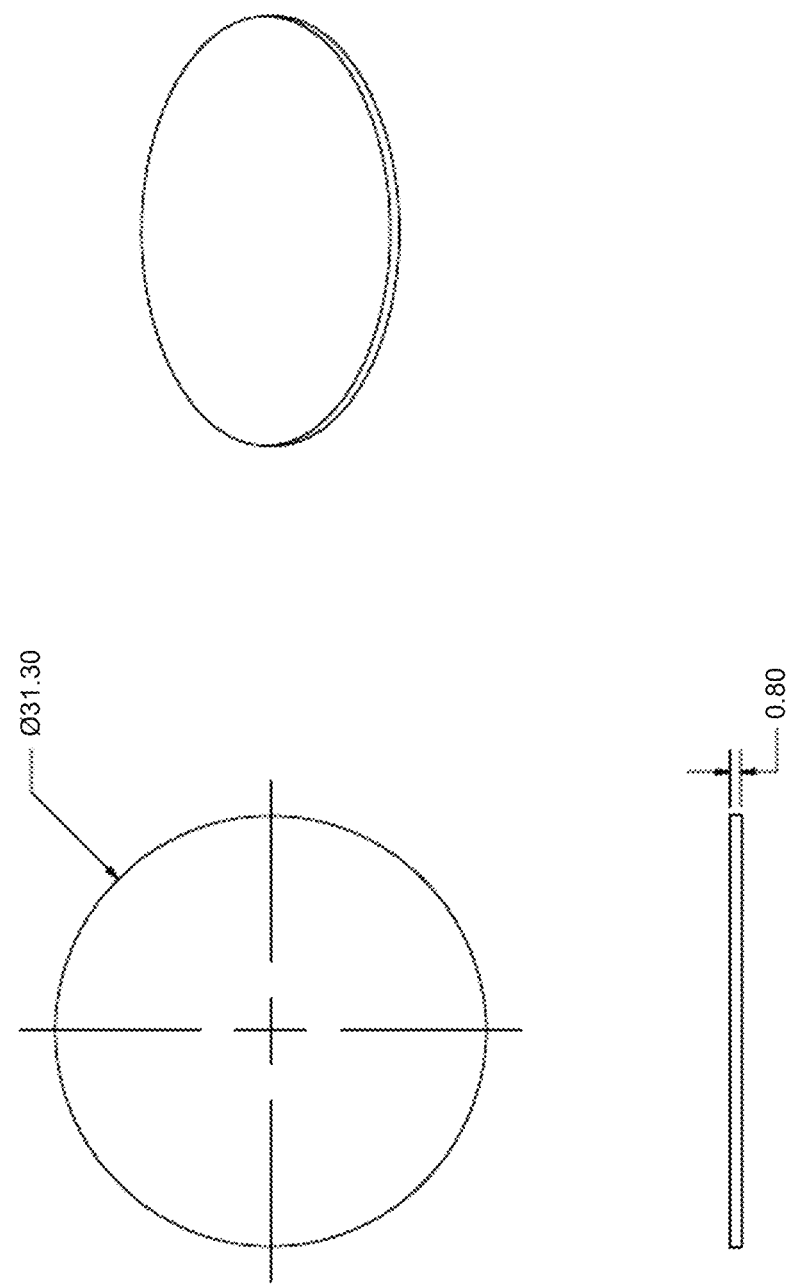

An exemplary device is shown in FIGS. 17A-17L. In this device, the light diffusing element is enclosed in an external housing without an external shell (FIGS. 17A, 17B, and 17D). The light diffusing element (FIG. 17I) is connected to a light conducting conduit (FIG. 17J) which is also connected to a light measuring component, a spectrometer as depicted (FIG. 17K). The light conducting conduit includes SMA connectors. As shown in section G of FIG. 17B and section D-D of FIG. 17F, the external housing has tiered recesses around the window to accommodate a filter (35), e.g., protective glass, and the screen (5). FIG. 17G shows a gasket that can be used to seal around a data port, e.g., mini USB, to seal the external housing from moisture. FIG. 17H shows a spacer used to ensure that the light conducting conduit is inserted into the light diffusing element at the correct depth.

Calibration and Methods of Use

The devices of the invention may be calibrated before use. This calibration may include transmitting a light beam (e.g., visible light, or infrared light, or UV light) from a calibrated lamp, e.g., a NIST certified lamp, into light diffusing element (1). The light source can be one that is capable of curing dental resin. A portion of this light is transmitted along light conducting conduit (33) into the light measuring component, e.g., spectrometer (32), that measure properties of the light and may then generate an indicator, and/or an additional communication step may occur where the data is communicated to an external processor (e.g., a computer) for analysis and/or indicator display. This indicator may be power, irradiance, or maximum exposure time. This indicator value is then compared against the anticipated indicator value for the calibrated light source. A correction factor may then be applied to the software and/or programming within the processor to generate an accurate light measurement. Alternatively, the value obtained by the devices of the invention may be compared to those obtained by an integrating sphere, and a correction factor applied accordingly.

In some embodiments, the devices of the invention may be used to test the properties, e.g., transmitted spectral power, transmitted light power, transmitted light intensity, and/or maximum safe exposure time, of light through a light blocking material (e.g., a shield or pair of glasses that protect against ocular damage from light generated by dental resin curing tools). Specifically, this light may be generated from a LCU. Filters, e.g., blue filters, neutral density, or short wave length, may optionally be used as appropriate to the light source. The safety material, e.g., safety glasses and/or shields, can be placed over the light diffusing element. The light may then be directed through the material into the light diffusing element for a duration and/or from a distance representative of the normal use of the light source. Other parameters may be used as required by the application, and, as discussed above, the device may be calibrated to each set of parameters if required. The light then diffuses within the light diffusing chamber, and a portion of the light exits the chamber through the port and is transmitted along the light conducting conduit to a light measuring component, where properties of the light are measured. This device then may analyze the data and render the required indicator and/or the data from measuring the properties of the light are communicated to an external processor for analysis and/or indicator display. This method is further discussed below in Example 1.

In still other embodiments, the devices of the invention may be used with other light generating sources and methods, e.g., those described in U.S. Pub. Nos. 2012-0171745, 2012-0172478, and 2012-0196122, each of which is hereby incorporated by reference in its entirety.

EXAMPLES

The following examples are intended to illustrate the invention. They are not meant to limit the invention in any way.

Example 1

Background:

Improperly polymerized dental resin materials have reduced mechanical, hardness, and structural integrity, which lead to reduced longevity, high replacement costs, and potential exposure to toxic unpolymerized materials. For instance, the average life of resin-based fillings is six years. A key aspect of light curing is that the dentist must watch at all times the restoration of the tooth. A high power 1 Watt) LCU cures the resin. Because the greatest ocular hazard to blue-light occurs at approximately 440 nm (which is close to the peak wavelength of many light emitting diode curing lights), the dentist must wear blueblocking glasses or shields to protect both his or her own eyes and the patient's eyes from the blue light and prevent retinal damage. The maximum daily exposure from a high power curing unit with an output of 1.56 $W/cm^2$ is only about 6 seconds when the dentist's eyes are 30 cm away from tooth.

Dental resin materials generally consist of light sensitive monomers that polymerize when properly initiated by light in a narrow range of the visible blue spectrum. Most lights units emit intense blue light in the 400-500 nm wavelength range with radiant power that can be in excess of 1 Watt. However, the spectral emissions are different between brands of LCUs, with some also emitting in the ultraviolet-A (UVA) range (320-400 nm). The ISO 10650-1 standard for halogen curing lights limits the irradiance in the 190 nm to 385 nm region to no more than 200 $mW/cm^2$, but there is no upper irradiance limit in the 400 to 500 nm range, and some units can deliver in excess of 10 $W/cm^2$, which can result in adverse health effects, especially ocular damage.

Figure 13:
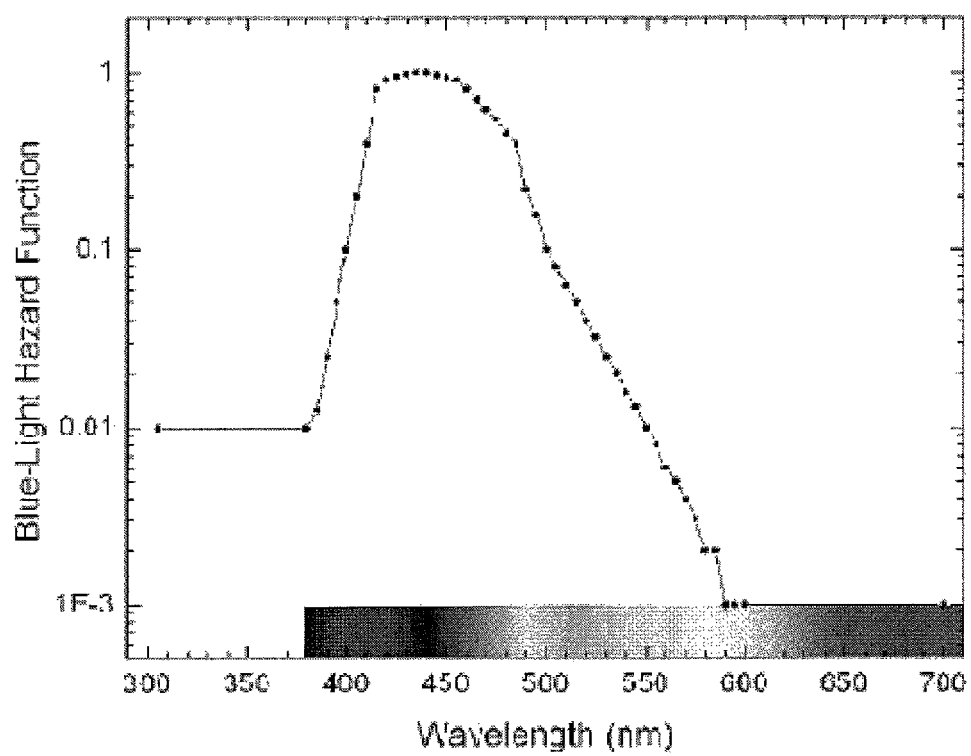
FIG. 13 is a graph showing the blue light hazard function for retinal photochemical damage at different wavelengths of light.
Figure 14A:
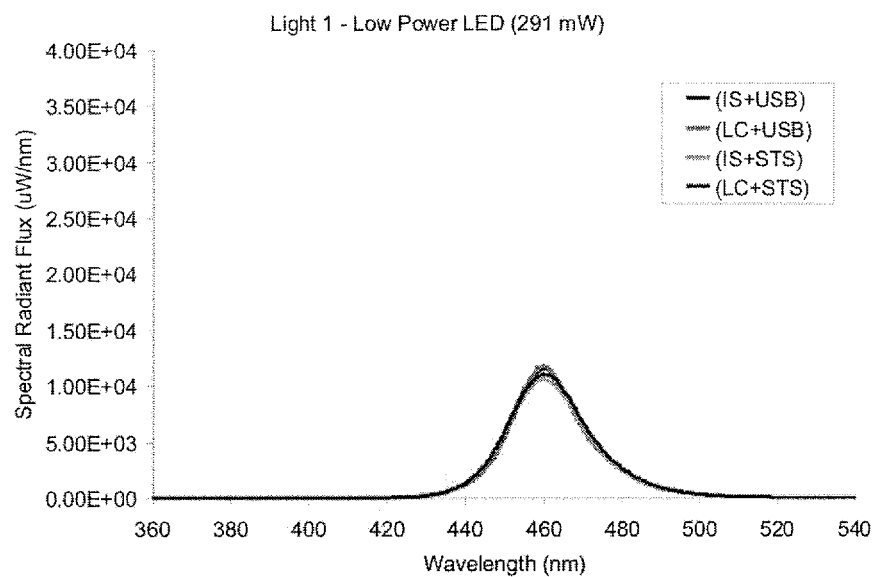
FIGS. 14A-D are a set of graphs showing spectral radiation flux of four different light sources of different powers (Light 1, Light 2, Light 3, and Light 4, respectively) measured using a light collector (device of the invention) or an integrating sphere (Labsphere, Inc., 6 in.). Two different spectrometers were used as indicated (USB-USB4000 and STS-STS vis, both from Ocean Optics).
Figure 14B:
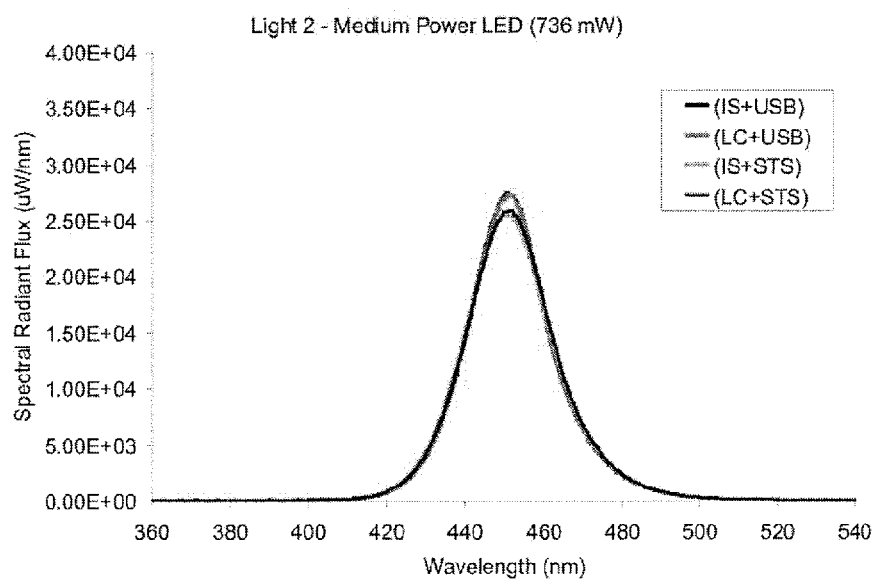
Figure 14C:
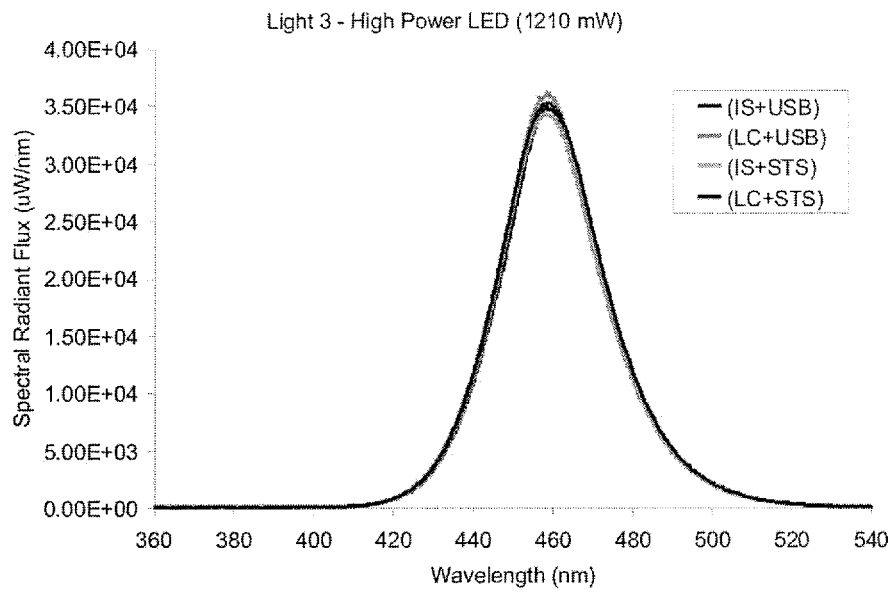
Figure 14D:
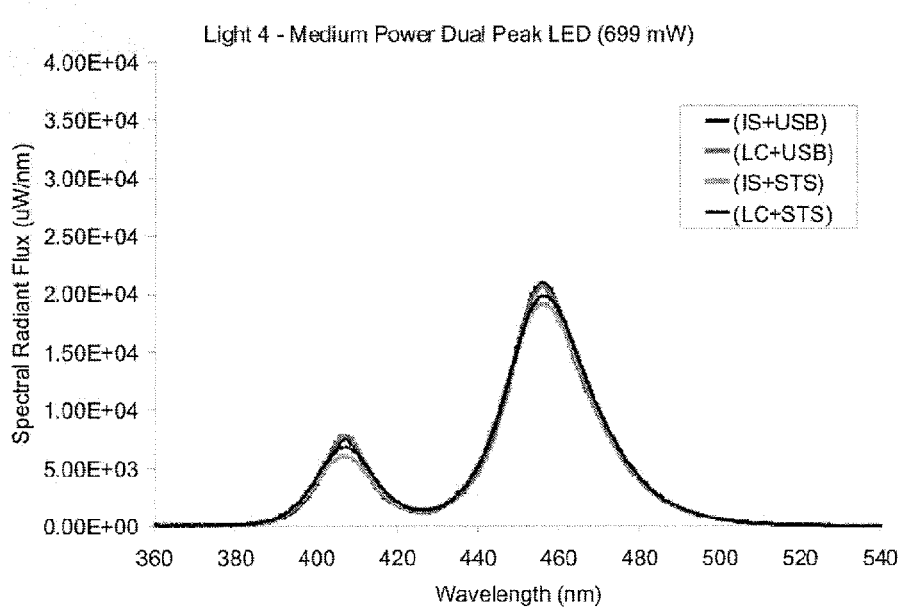
Figure 16A:
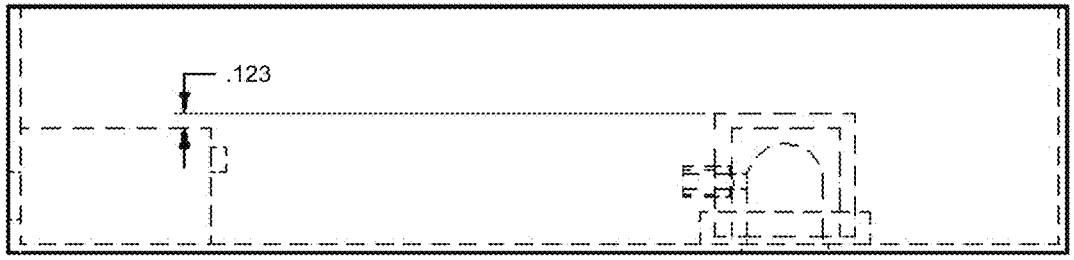
FIG. 16A is a schematic diagram of side view of a fully assembled device of the invention showing the relative position of the various parts of the device. Units are in inches.
Figure 16B:
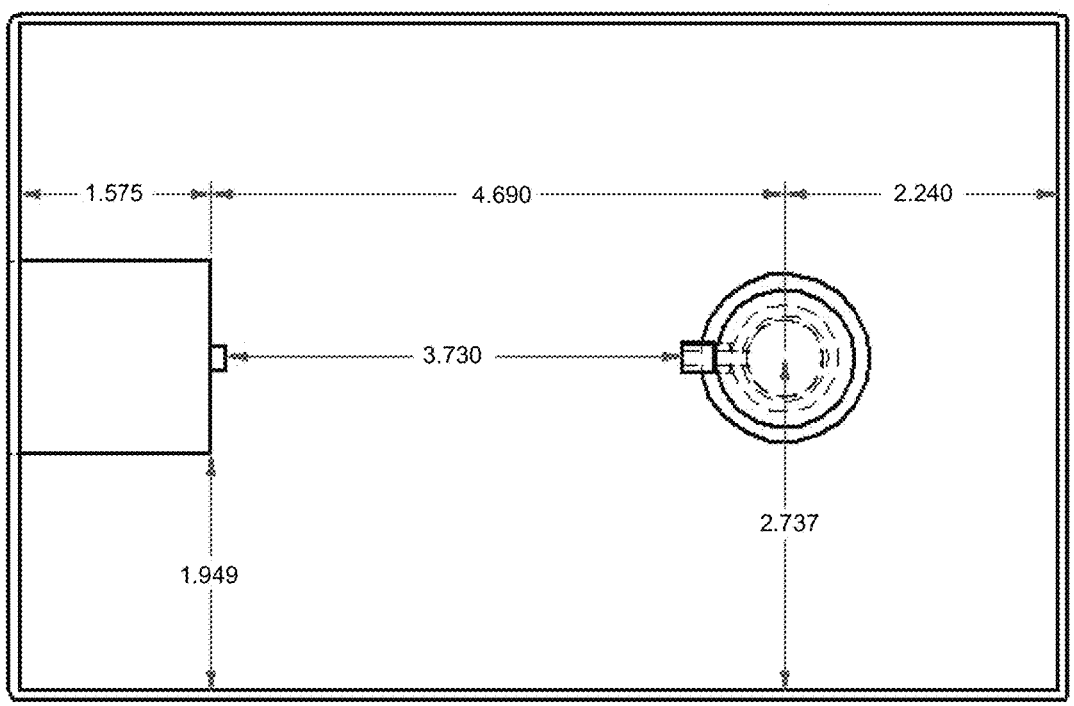
FIG. 16B is a schematic diagram of top view of a fully assembled device of the invention showing the relative position of the various parts of the device. Units are in inches.

FIG. 13 shows the blue light hazard function for retinal photochemical damage (American Conference of Government Industrial Hygienists; TLVs and BEIs based on the Documentation of the Threshold Limit Values for Chemical Substances and Physical Agents and Biological Exposure Indices; 2008, pp 146-154). The function is greater than 0.1 in the spectral range from 400 nm to 500 nm. The greatest ocular hazard to blue-light occurs at approximately 440 nm (which is close to the peak wavelength of many light emitting diode curing lights). Blue light transmits through the ocular media and is absorbed by the retina; at chronic low levels of exposure, the blue light amplifies retinal aging and degeneration by causing photochemical injury to the retinal-pigmented epithelium and choroid. Clinical manifestations of retinal damage include acute photoretinitis or, in severe cases, premature age-related macular degeneration.

Experimental Methods:

A device of the invention, as shown in FIGS. 2A-2C and FIGS. 16A-16B, was tested. This device included a light collector connected to a spectrometer and encased within an external housing. The spectrometer used was an STS-VIS spectrometer that is optimized in the visible region with a slit width of 200 µm and a fiberoptic cable with a core diameter of 400 µm and a length of 10 cm. Protective eyewear/shields were placed over the window of the external housing. An LCU, in particular a dental curing wand, was held approximately 30 cm away from the protective eyewear/shield. The inner surfaces of the light diffusing element were made of polytetrafluoroethylene (Teflon®).

LabVIEW was used as an exemplary programming language to collect the spectra measured by the device and to calculate the maximum exposure time. Inputs for data collection and analysis include integration time, LCU type (PAC, QTH, or LED) and distance between the operator and the tooth. A "dark" spectrum was measured first with the LCU off, and then the transmitted spectrum with the LCU on was measured. The raw and blue-weighted spectra were used to verify that the data collection has been carried out correctly and to provide a visual guide on the signal to noise ratio in the spectra.

Figure 9:
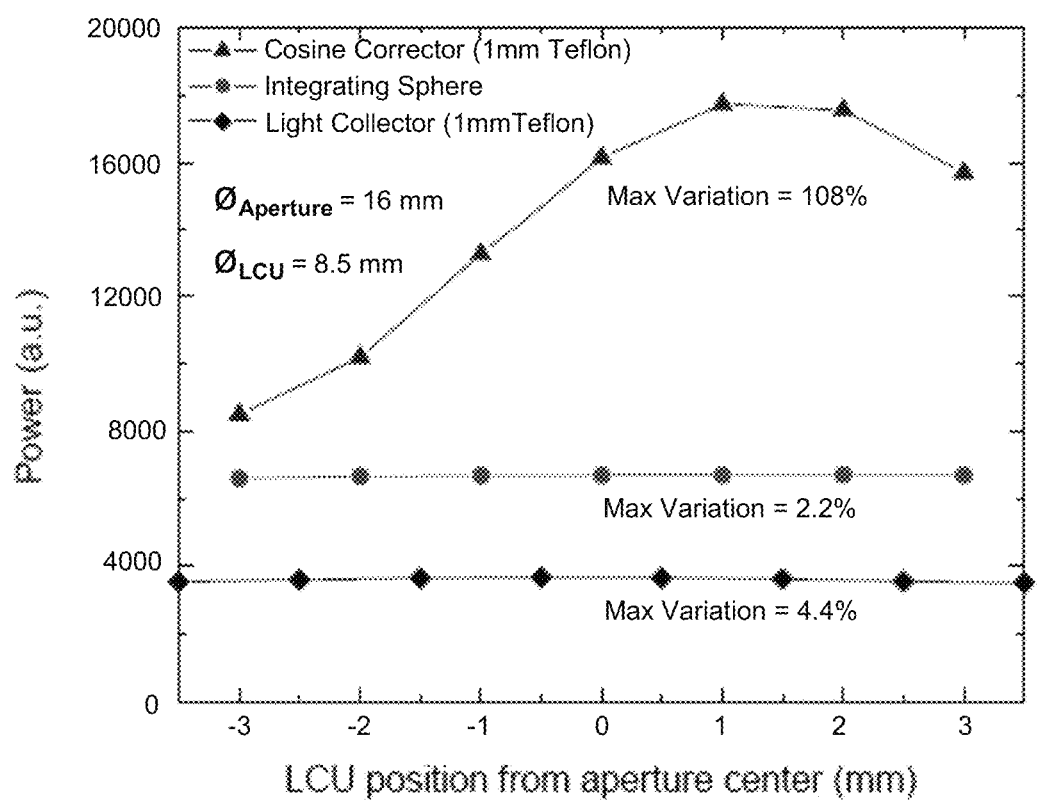
FIG. 9 is a graph showing a comparison of power and power variation between three different light collecting devices, measured using a STS spectrometer.

Results:

FIG. 9 displays a comparison between different light collecting devices that were measured using a STS spectrometer. The radiant source was an LED based "Allegro" light curing unit. Both the Cosine Corrector (Ocean Optics) and the Light Collector of the present invention had a 1 mm thick polytetrafluoroethylene (Teflon®) piece covering their apertures. The "Integrating Sphere" refers to the Ocean Optics FOIS-1 Fiber Optic Integrating Sphere (Ocean Optics, 3 in.). An ideal device has the highest power and smallest power variation across LCU position from aperture center, as well as lowest cost. The smallest power variation was key for this application.

During testing, it was noted that when an LCU was shining through blue blocker glasses or shields, fluorescence with wavelengths greater than 500 nm was emitted from the glasses or shields. This fluorescence entered and scattered within the spectrometer, resulting in a spurious signal in the spectral range below 500 nm. This spurious signal interfered with the weakly transmitted blue light. A blue band pass filter was necessary to attenuate the fluorescence.

Figure 10:
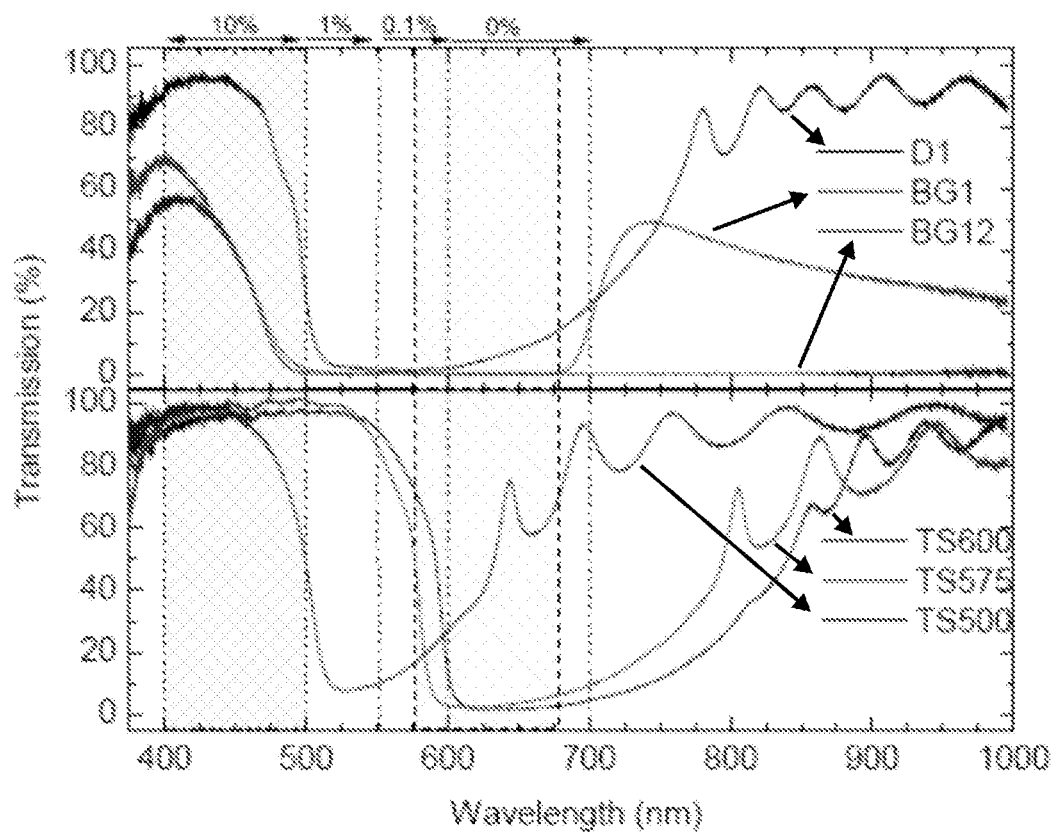
FIG. 10 is a graph showing transmission spectra of interference (TS600, TS575, TS500, and D1) and color (BG1 & BG12) filters measured by an Ocean Optics USB4000 spectrometer through an Ocean Optics FOIS-1 Fiber Optic Integrating Sphere.

FIG. 10 depicts transmission spectra of interference (TS600, TS575, TS500, and D1) and color (BG1 & BG12) filters measured by an Ocean Optics USB4000 spectrometer through an Ocean Optics FOIS-1 Fiber Optic Integrating Sphere (Ocean Optics, 3 in.). The reference light source is an incandescent light bulb (60 W; 120V). The ideal filter allows 100% of the light within the blue region and 0% within the yellow region. In the present Example, the results indicate that the color BG1 filter is optimal for this application.

Figure 11:
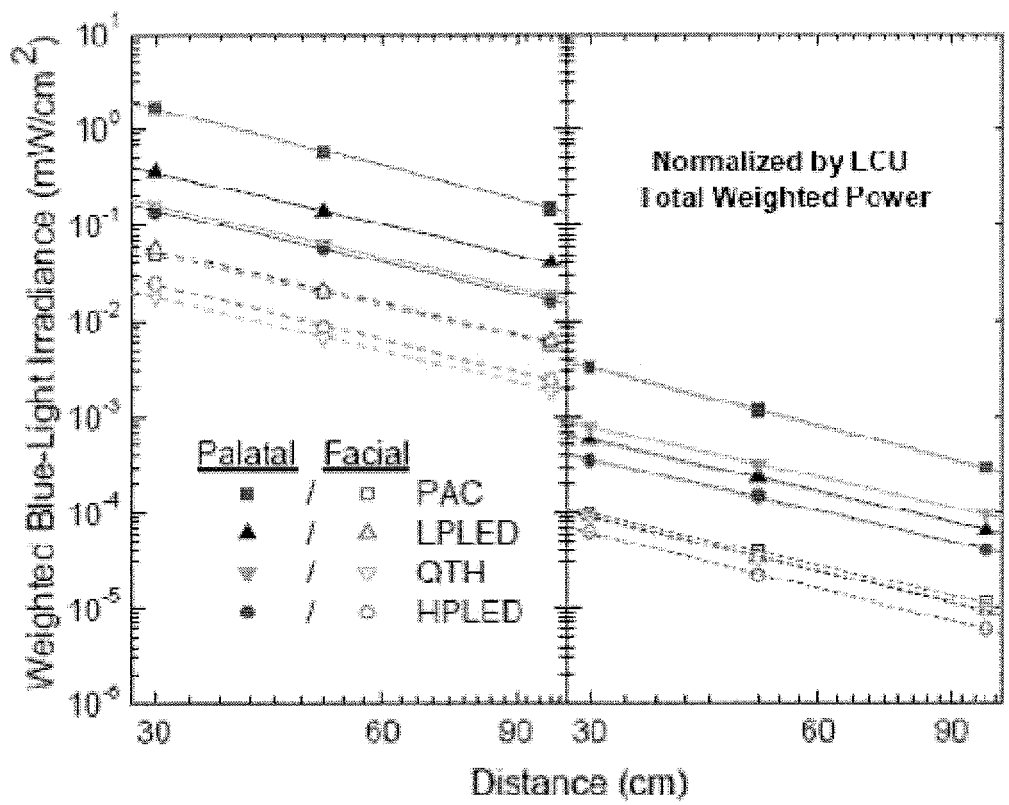
FIG. 11 is a set of graphs displaying data of weighted blue light irradiance as a function of distance from a LCU for the palatal and facial geometries. The graph on the right displays least-square fitted lines of the data.

FIG. 11 displays data of weighted blue light irradiance as a function of distance from an LCU for the palatal and facial geometries. The data were obtained from the literature (Evaluation of ocular hazards from 4 types of curing lights, Labrie D, Moe J, Price R B, Young M E, Felix C M. *J. Can. Dent. Assoc.* 2011; 77:b116) under typical clinical conditions. These data were used to evaluate the total weighted power as a function of distance for the two geometries. As shown in FIG. 11 (right), the data were least-square fitted by straight lines. The equations are shown below:

$$WI = WP \cdot C \cdot d^B,$$

and $$C = 10^A.$$

WI is the weighted irradiance in units of $\mu W/cm^2$, WP is the weighted power in units of $\mu W$ calculated from the spectral radiant power transmitted through the glasses and shields and measured by the prototype device, d is the distance between the eyes and the LCU in units of cm, and A and B are two parameters given in Table 1.

TABLE 1

| Constant | Palatal | | | Facial | | |
|---|---|---|---|---|---|---|
| | LED | QTH | PAC | LED | QTH | PAC |
| A | −0.53602 | −0.77749 | 0.48787 | −1.30516 | −1.34564 | −1.3718 |
| B | −1.78566 | −1.80626 | −2.0141 | −1.858965 | −1.9413 | −1.78902 |

The maximum acceptable exposure time, $t_{max}$, may be determined as follows:

$$t_{max} = \frac{E_{limit}}{WI}$$

where $E_{limit}$ is equal to 10000 $\mu J/cm^2$.

Evaluation of the Effectiveness of Blueblocker Protective Glasses/shields against Ocular Light Induced Hazards Table 2 shows a list of seven shields and eight blueblocker glasses together with two glasses (A1 and A2) used in the glass blowing industry.

TABLE 2

| ABBRE-VIATION | MODEL NAME | LENS | MFG# | MANU-FACTURER |
|---|---|---|---|---|
| S1 | Pinnacle Vision Saver | — | 4575 | TotalCare Corporation[1] |
| S2 | Round Orange Blockers | — | Inc. w/ Kerr Sybron Command | Kerr Corporation[1] |
| S3 | Cure-Shield | — | 9006166 | Premier Dental Products[2] |
| S4 | Shield VLC Angulate | — | 089-4550 | Patterson Dental Supply[3] |
| S5 | Swiss Master Light | — | DT-072 | EMS[4] |
| S6 | Protective light shield | — | 20816 | Kerr Corporation[1] |
| S7 | Orange Shields (Large) | — | 5600011 | Patterson Dental Supply[3] |
| G1 | Light protection goggles | — | DZ-011 | EMS[4] |
| G2 | Genesis XC?[7] | Orange (2-1.7 U 1 FT K N CE/ 3111) | ?[7] | Ultraden/uvex?[7] |
| G3 | Filter Argon/KTP-EN207 | 60 (Orange) | ?[7] | NoIR[5] |
| G4 | Ultra-spec 1000 (140 mm Z87) | Orange | ?[7] | Uvex[6] |
| G5 | super fit | PC amber/ UV 2-1.2 | 9178.385 | Uvex[6] |
| G6 | Ultra-spec 2000 (130-150 mm Z87.1) | SCT-Orange | S0360X | Uvex[6] |
| G7 | skyper | SCT-Orange | S1933X | Uvex[6] |
| G8 | Style #21 - Large Flip-up Clip-ons | #60 | #21 #60 | NoIR[5] |
| A1 | Astrospec OTG 3001 | Shade 3.0 Infra-dura | S2508 | Uvex[6] |
| A2 | Astrospec OTG 3001 | Shade 5.0 Infra-dura | S2509 | Uvex[6] |

[1]1717 West Collins, Orange, CA 92867 (totalcareprotects.com/kerrdental.com)
[2]1710 Romano Drive, Plymouth Meeting, PA 19462, U.S.A. (premusa.com)
[3]1205 Henri Bourassa Blvd., W. Montreal, Quebec, Canada, H3M 3E6 (pattersondental.ca)
[4]Ch. de la Vuarpillière 31, 1260 Nyon, Switzerland (ems-company.com)
[5]6155 Pontiac Trail, South Lyon, MI 48178 (noir-medical.com/noirlaser.com)
[6]UVEX ARBEITSSCHUTZ GmbH, Würzburger Str. 181-189, 90766 Fürth (uvex.com)
[7]The question marks indicate insufficient information was available to fully describe the glasses/shields.

Figure 12:
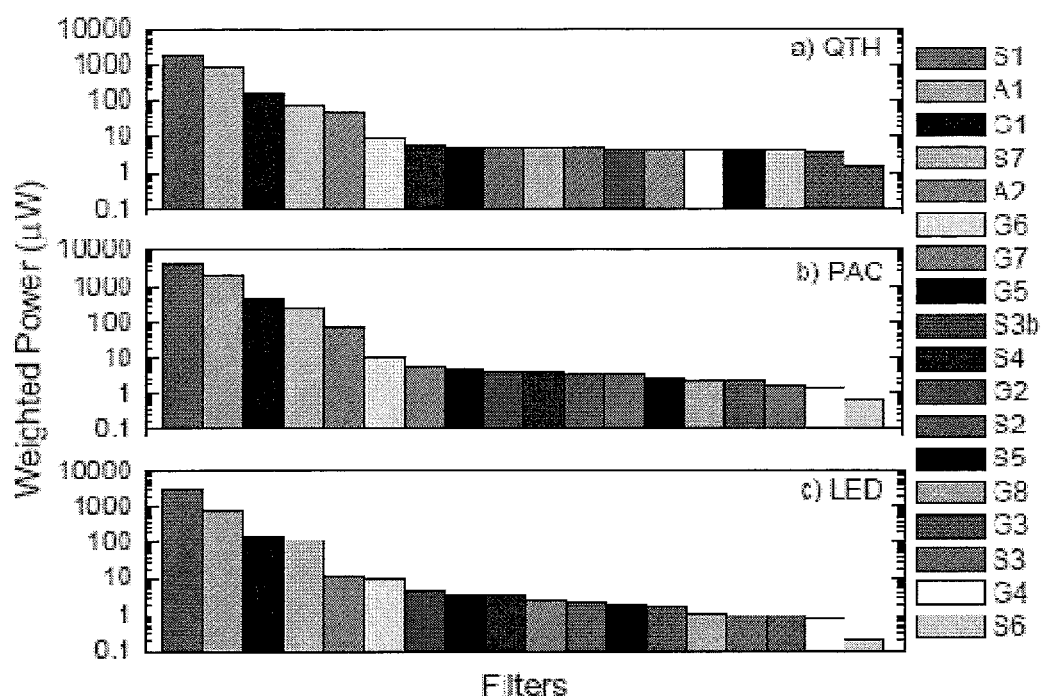
FIG. 12 is a graph showing the weighted power for all shields and using QTH, PAC, or LED light curing units as light sources.

FIG. 12 illustrates the weighted power for all shields and glasses (Table 2) tested in this Example, with QTH, PAC, and LED light curing units as light sources. The highest weighted power of 5 mW was collected using a PAC LCU and S1 shield, while the lowest power of 0.2 $\mu W$ was collected using a LED LCU and S6 shield. These measurements provide evidence of the dynamic range and sensitivity available with the device.

Conclusion:

The device and methods tested and described in the present Example were highly effective in functioning as a means to evaluate the effectiveness of protective eyewear/shields using the light curing units found in dental clinics.

Example 2

Experimental Objective:

To demonstrate that a device of the invention (light collector) accurately measures spectral radiant flux, of four different light sources, as compared to a commercially available integrating sphere (Labsphere Inc., 6 in.).

Experimental Method:

Equal amounts of light from four different light sources were introduced into either a device of the invention (as shown in FIGS. 2A-2C and FIGS. 7A-7C) or an integrating sphere (Labsphere Inc., 6 in.). Spectral radiance flux across 360 nm-540 nm wavelengths was measured and recorded for each light source.

Results:

The device of the invention collected and measured data accurately, from each light source, as compared to a commercially available integrating sphere (Labsphere Inc., 6 in.). Data for total spectral radiant flux measurements from each of the light sources, using the device of the invention or the integrating sphere (Labsphere Inc., 6 in.) are provided in Table 3 and in FIGS. 14A-14D.

TABLE 3

Total Spectral Radiant Flux

| Measurement Device | Spectrometer | Light 1 (mW) | Light 2 (mW) | Light 3 (mW) | Light 4 (mW) |
|---|---|---|---|---|---|
| Integrating Sphere (IS) | USB4000 | 287 | 740 | 1189 | 699 |
| Integrating Sphere (IS) | STS | 288 | 731 | 1204 | 689 |
| Light Collector (LC) | USB4000 | 291 | 734 | 1210 | 694 |
| Light Collector (LC) | STS | 298 | 739 | 1238 | 714 |
|  | Mean | 291 | 736 | 1210 | 699 |
|  | S.D | 5 | 4 | 21 | 11 |
|  | Variance (%) | 1.7% | 0.6% | 1.7% | 1.5% |

Light 1: Smartlite IQ (Denstply Caulk);
Light 2: Elipar S10 (3M ESPE);
Light 3: D1 (DXM);
Light 4: Bluephase Style (Ivoclar Vivadent)

Conclusion:

The device of the invention accurately measured spectral radiant flux, and these measurements are comparable to those made by a commercially available integrating sphere (Labsphere Inc., 6 in.).

All publications and patents cited in this specification are incorporated herein by reference as if each individual publication or patent were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A device comprising:
   a) a light diffusing element comprising:
      an element comprising a top portion, a bottom portion, and a side portion, wherein said top portion comprises a screen, said bottom portion comprises an inner surface that is substantially hemispherical, and said side portion comprises an inner surface that is substantially cylindrical, and wherein said side portion is connected to said top portion and said bottom portion; and
      an outlet port in said side portion, wherein said outlet port is substantially parallel to said top portion and is adjacent to said bottom portion, and wherein said outlet port is configured to receive a light conducting conduit,
   wherein said light diffusing element prevents light from penetrating through said side portion or said bottom portion.

2. The device of claim 1, further comprising:
   b) a light measuring component comprising an opening configured to receive the light conducting conduit; and
   c) the light conducting conduit comprising a first end and a second end, wherein said first end is optically connected to said outlet port of said light diffusing element, and said second end is optically connected to said opening in said light measuring component.

3. The device of claim 2, wherein said device further comprises an external housing enclosing said light diffusing element, said light measuring component, and said light conducting conduit.

4. A method for measuring light, comprising directing light generated by a light source into the light diffusing element of a device of claim 2, wherein
   a) light entering said light diffusing element diffuses within said light diffusing element;
   b) a portion of said light diffused within said light diffusing element exits through said outlet port and is transported through said light conducting conduit to said light measuring component;
   c) said light measuring component collects data from said light of step (c) and transmits said data to a processor; and
   d) said processor analyzes said data and generates an indicator.

5. The method of claim 4, wherein said light measuring component measures visible light, infrared light, or UV light.

6. The method of claim 4, wherein said indicator is power, irradiance, or maximum exposure time.

7. The method of claim 4, wherein said method further comprises a calibration step comprising:
   e) providing a pre-calibrated lamp;
   generating a light beam from said pre-calibrated lamp and directing said light beam into said light diffusing element;
   g) obtaining an indicator value and comparing said value to an indicator value associated with said pre-calibrated lamp; and
   h) determining a correction factor based on said comparing in step (g); and
   i) applying said correction factor in generating said indicator in step (d).

8. The device of claim 1, wherein said light diffusing element is enclosed within an external shell comprising an inner wall and an outer wall and further comprising a connecting element aligned with said outlet port and further aligned with said first end of said light conducting conduit.

9. The device of claim 8, wherein said inner surface of said side portion of said light diffusing element is separated from said inner wall of said external shell by between 1 mm and 15 mm.

10. The device of claim 8, wherein said inner surface of said side portion of said light diffusing element is separated from said inner wall of said external shell by a distance that is sufficient to prevent light from penetrating said inner surface of said side portion or said bottom portion of said light diffusing element and interacting with said inner wall of said external shell.

11. The device of claim 1, wherein said element comprising the top portion, the bottom portion, and the side portion allows for substantially uniform light diffusion across said inner surfaces.

12. The device of claim 11, wherein said inner surfaces comprise polytetrafluoroethylene, titanium dioxide-coated alumina, or polyoxymethylene.

13. The device of any claim 1, wherein said top portion further comprises an aperture having a diameter substantially equivalent to or smaller than the diameter of said substantially cylindrical inner surface of said side portion, and wherein said screen covers said aperture.

14. The device of claim 13, wherein said aperture in said top portion of said light diffusing element has a diameter between 4 mm and 30 mm.

15. The device of claim 1, wherein said screen is substantially square, circular, or disc-shaped and is sized so as to cover said side portion of said light diffusing element.

16. The device of claim 1, wherein said screen comprises polytetrafluoroethylene, titanium dioxide-coated alumina, or polyoxymethylene.

17. The device of claim 1, wherein said screen further comprises a one-way mirror, wherein said one-way mirror allows light into said light diffusing element but substantially blocks light from exiting said light diffusing element through said one-way mirror.

18. The device of claim 1, wherein the height of said substantially cylindrical inner surface of said side portion is between 1 mm and 50 mm.

19. The device of claim 1, wherein said light conducting conduit has an inner diameter between 10 μm and 1000 μm.

20. The device of claim 1, wherein said opening of said light measuring component is between 10 μm and 1000 μm in diameter.

21. The device of claim 1, wherein said light measuring component is capable of measuring wavelengths between 150 nm and 1000 nm.

22. The device of claim 1, wherein said device further comprises a processor to which data collected by said light measuring component is transmitted for analysis.

* * * * *